United States Patent [19]

Bollinger

[11] 4,411,688

[45] Oct. 25, 1983

[54] SUBSTITUTED 2-IMINO-1,3-DITHIO AND 1,3-OXATHIO HETEROCYCLIC COMPOUNDS AS HERBICIDAL ANTIDOTES

[75] Inventor: Frederic G. Bollinger, Creve Coeur, Mo.

[73] Assignee: Monsanto Company, St. Louis, Mo.

[21] Appl. No.: 341,432

[22] Filed: Jan. 21, 1982

Related U.S. Application Data

[62] Division of Ser. No. 170,505, Jul. 21, 1980, Pat. No. 4,321,082, which is a division of Ser. No. 960,987, Nov. 15, 1978, Pat. No. 4,231,783.

[51] Int. Cl.³ .................... A01N 43/02; A01N 37/18
[52] U.S. Cl. .......................................... 71/90; 71/118
[58] Field of Search ............... 71/90, 100, 118; 549/21, 38, 89

[56] References Cited

U.S. PATENT DOCUMENTS

| | | | |
|---|---|---|---|
| 3,131,509 | 5/1964 | Hoffmann | 71/77 |
| 3,389,148 | 6/1968 | Lies | 549/21 |
| 3,433,803 | 3/1969 | Ottmann et al. | 71/90 |
| 3,449,365 | 6/1969 | Lies | 260/455 A |
| 3,449,366 | 6/1969 | Lies | 260/455 A |
| 3,449,493 | 6/1969 | Addor | 71/90 |
| 3,484,455 | 12/1969 | Addor | 71/90 |
| 3,755,363 | 8/1973 | Timmons et al. | 71/90 |
| 4,021,224 | 5/1977 | Pallos et al. | 71/100 |
| 4,101,307 | 7/1978 | Clapot et al. | 71/90 |
| 4,231,783 | 11/1980 | Bollinger | 71/90 |
| 4,321,082 | 3/1982 | Bollinger | 71/90 |
| 4,342,586 | 8/1982 | Bollinger | 71/90 |

FOREIGN PATENT DOCUMENTS

| | | | |
|---|---|---|---|
| 5435218 | 3/1959 | Japan | 71/90 |
| 49-35272 | 9/1974 | Japan | 71/90 |

*Primary Examiner*—Glennon H. Hollrah
*Attorney, Agent, or Firm*—Richard H. Shear; Patricia A. Coburn; J. Timothy Keane

[57] ABSTRACT

Derivatives of 2-imino-1,3-dithiolane, 1,3-dithiole, 1,3-dithiane, 1,3-dithietane and 1,3-oxathiole have been found to reduce herbicidal injury to crop plants due to thiocarbamate and acetanilide herbicides.

39 Claims, No Drawings

SUBSTITUTED 2-IMINO-1,3-DITHIO AND 1,3-OXATHIO HETEROCYCLIC COMPOUNDS AS HERBICIDAL ANTIDOTES

This is a division of application Ser. No. 170,505 filed July 21, 1980 now U.S. Pat. No. 4,321,082 which is a division of Ser. No. 960,987 filed Nov. 15, 1978, now U.S. Pat. No. 4,231,783.

This invention relates to novel 2-imino-1,3-dithio and 1,3-oxathio heterocycles and derivatives thereof as well as their use in compositions and methods for reducing herbicidal injury. More specifically, the invention relates to novel compositions and methods for reducing injury to crop plants by herbicides such as thiocarbamates and acetanilides, which comprises treating the crop plant locus or the seed of the crop plant with an effective amount of compounds which will be described more fully below.

BACKGROUND OF THE INVENTION

Herbicides are widely used to control weed growth in growing crop plants. Unchecked weed growth is detrimental to the crop plant because weeds compete with crop plants for light, water and various nutrients. This can result in lower crop yields as well as poorer crop quality. The presence of weeds in a growing crop also interferes with the cultivation and harvesting of the crop plant. Among the commercially available herbicides, thiocarbamates and acetanilides have proven to be effective in controlling various weed pests. Unfortunately, thiocarbamate and acetanilide herbicides can also cause serious injury to some crop plants at application rates necessary to stunt or kill weeds. A compound or composition which protects the crop plant from the action of the herbicide, without reducing the herbicidal effectiveness against the weed to be controlled, would be beneficial.

Compounds which are useful in reducing or eliminating crop injury are variously referred to by those skilled in the art as antidotes, safeners or antagonistic agents. It has been found that certain 2-imino derivatives of 1,3-dithiolane, 1,3-dithiole, 1,3-dithiane, 1,3-dithietane and 1,3-oxathiole are effective safening agents. Certain of these compounds are known in the art; the following patents are representative of the art in this area.

U.S. Pat. No. 3,449,365 discloses 2-imino-4-alkalidene-1,3-dithiolanes and teaches that said compounds are useful as insecticides, acaricides and nematocides. U.S. Pat. No. 3,449,366 discloses 2-amino-4,5-substituted-1,3-dithioles which are useful as insecticides. U.S. Pat. No. 3,389,148 discloses processes for preparing substituted 1,3-dithioles, 1,3-dithianes, 1,3-dithiolanes and the salts thereof which are intermediates in the preparation of phosphorylated imino compounds. U.S. Pat. Nos. 3,189,429 and 3,139,439 disclose the preparation and herbicidal use of the halide salts of 2-dialkylamino-1,3-dithiolane derivatives. British Pat. No. 1,367,862 discloses substituted phenyl-2-imino-1,3-dithietanes which are chemosterilants of adult female Ixodides. U.S. Pat. No. 4,025,532 discloses 2-(o-tolyl)imino-1,3-dithioles which are Ixodides. None of the above patents teach or suggest that the substituted 2-imino-1,3-dithio and 1,3-oxathio heterocyclic compounds of the present invention would be useful as herbicidal antidotes.

DESCRIPTION OF THE INVENTION

It has been found that various crop plants can be protected against the herbicidal action of thiocarbamate and acetanilide herbicides, without a corresponding reduction in injury to the weeds, by the application to the crop plant locus or the seed of the crop plant prior to planting of an effective safening amount of a compound having the formula

R-N=A or an agriculturally acceptable acid addition salt thereof, wherein R is hydrogen, lower alkyl, or

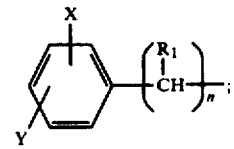

$R_1$ is hydrogen or lower alkyl; X and Y independently equal hydrogen, lower alkyl, lower alkoxy or halogen; n is 0, 1, 2 or 3; A is

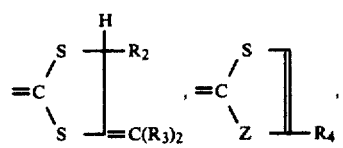

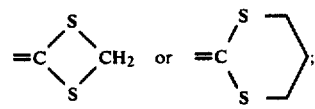

$R_2$ is hydrogen or methyl; $R_3$ is hydrogen or halogen; $R_4$ is hydrogen, methyl or phenyl; Z is oxygen or sulfur; provided that when n is 1 and A is

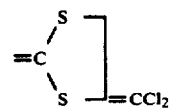

$R_1$ cannot equal ethyl and when n is 1 and A is

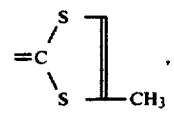

$R_1$ cannot equal n-propyl or isobutyl.

It is believed that compounds described by the above formula are novel except where R equals hydrogen, where A equals

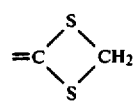

or where A equals

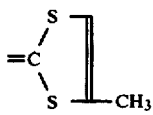

and n equals 0.

Preferred compounds employed in the invention are those in which R is

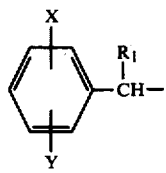

and A is

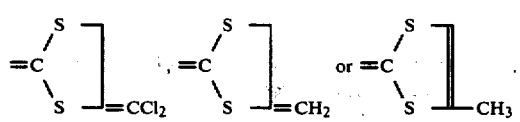

Among the above-described preferred compounds, the most preferred are those in which $R_1$ is methyl and X and Y are hydrogen.

As used herein the term "lower alkyl" includes those members including straight and branched chain, having from 1 to 5 carbon atoms inclusive, for example, methyl, ethyl, n-propyl, isopropyl, n-butyl, sec-butyl, tert-butyl, n-pentyl, isopentyl and the like. The term "lower alkoxy" includes straight and branched chain members having from 1 to 5 carbon atoms, inclusive, for example, methoxy, ethoxy, isopropoxy and the like. The term "halogen" or "halo" is understood to include chlorine, bromine, fluorine and iodine atoms, preferably chlorine.

The agriculturally acceptable acid addition salts of the compounds of the foregoing formula are derived from "strong acids" which is understood herein to mean those inorganic and organic acids having a dissociation constant equal to or greater than about $5 \times 10^2$, for example, hydrochloric acid, hydrobromic acid, hydroiodic acid, sulfuric acid, tri-halogenated acetic acid, oxalic acid and the like. Preferred salts are those derived from the hydrohalic acids, especially hydrochloric acid.

"Antidote", "safener" or "antagonistic agent" when used herein, refer to compounds which counteract the herbicidal action of a herbicide on a crop plant thereby reducing or eliminating injury to the crop plant without reducing the effectiveness of the herbicide against the weed(s) to be controlled.

The "antidotes" of the present invention are particularly advantageous for cereal crop plants of the grass family (Gramineae), for example, oats, wheat, barley, rye, corn, rice and sorghum, preferably rice, sorghum and wheat.

Exemplary of the thiocarbamate herbicides useful herein is S-(2,3,3-trichloroallyl) diisopropylthiocarbamate, S-(2,3-dichloroallyl) diisopropylthiocarbamate, S-ethyl diisopropylthiocarbamate, S-propyl dipropylthiocarbamate and the like. The antidotes of the present invention are preferentially employed as safeners for S-(2,3,3-trichloroallyl) diisopropylthiocarbamate, commonly known as triallate.

Exemplary of the acetanilide herbicides is 2-chloro-2',6'-diethyl-N-(methoxymethyl) acetanilide, commonly known as alachlor, 2-chloro-2',6'-diethyl-N-(butoxymethyl) acetanilide, commonly known as butachlor, 2-chloro-N-isopropylacetanilide, commonly known as propachlor, and the like. Among the acetanilide herbicides, the antidotes of the present invention are preferentially employed as safening agents for alachlor and butachlor.

The amount of safening agent employed in the methods and compositions of the invention will vary depending upon the particular herbicide with which the agent is employed, the rate of application of the herbicide, the crop to be protected as well as the manner of application of the safening agent. In each instance, the amount employed is a safening effective amount, i.e., the amount which reduces crop injury by thiocarbamate or acetanilide herbicides.

The safening agent may be applied to the plant locus in a mixture with the herbicide, sequentially, or it may be applied directly to the seed of the crop plant. By application to the "plant locus" is meant application to the plant growing medium, such as the soil, as well as the seeds, emerging seedlings, roots, stems, leaves, flowers, fruits or other plant parts.

The amount of herbicide employed is well within the skill of the art and is disclosed in various patents. Alachlor and butachlor and their herbicidal use is disclosed in U.S. Pat. Nos. 3,442,945 and 3,547,620. Propachlor and its herbicidal use is disclosed in U.S. Pat. No. 2,863,752 and Reissue 26,961. Triallate and diallate and their herbicidal use are disclosed in U.S. Pat. Nos. 3,330,643 and 3,330,821. Additionally, as is well known by those skilled in the art, the labels of commercially available thiocarbamate and acetanilide herbicides contain a complete description of the amount of herbicide to be employed to control the desired weed(s).

PREPARATION OF THE COMPOUNDS OF THE INVENTION

The substituted 2-imino-1,3-dithio- and oxathioheterocycles of the present invention are sulfur containing heterocycles generally known in the art as 1,3-dithiolanes, 1,3-dithioles, 1,3-dithianes, 1,3-oxathioles and 1,3-dithietanes.

The 1,3-dithiolanes of the invention are prepared according to several methods. The substituted 2-imino-4-dichloromethylene-1,3-dithiolanes may be prepared by cyclizing the appropriate 2,3,3-trihaloallyl N-substituted dithiocarbamate in the presence of a suitable solvent, for example, carbon tetrachloride, chloroform or toluene. When 2,3,3-trichloroallyl N-substituted dithiocarbamate is used, the reaction may be graphically illustrated as:

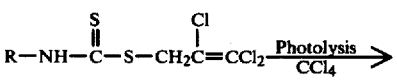

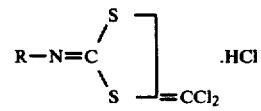

Substituted 2-imino-4-methylene-1,3-dithiolanes may be prepared by reacting an amine, such as α-methylbenzylamine with an alkynyl halide containing 3 or 4 carbon atoms. The reaction may be graphically illustrated as

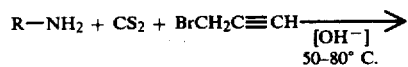

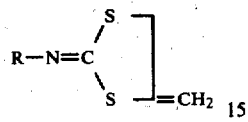

or

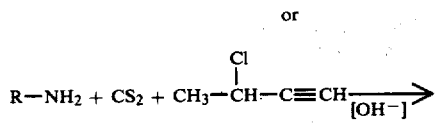

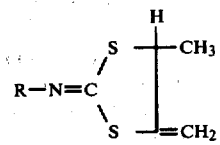

These compounds may also be prepared by reacting approximately equimolar quantities of a substituted 2-propynyl dithiocarbamate with a non-oxidizing strong acid, such as hydrochloric. The overall reaction may be graphically written as:

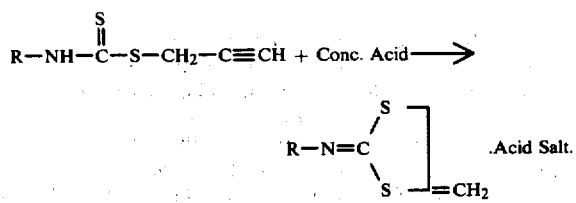

The substituted 2-imino-4-methyl-1,3-dithioles may be prepared by reacting chloroallyl N-substituted dithiocarbamate with a non-oxidizing strong acid, such as hydrochloric or hydroiodic, etc. The reaction may be carried out in an inert inorganic or organic medium such as water, alcohol or a mixture of the same. It is generally preferably to employ an excess of acid.

The reaction may be illustrated as follows:

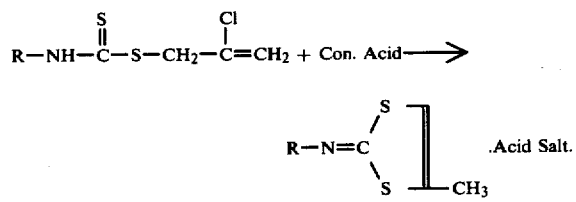

The substituted 2-imino-1,3-oxathioles of the invention may be prepared by reacting approximately equimolar portions of 1-substituted-3,3-dimethylthiourea and an appropriate halogenated aldehyde or ketone in an inert solvent such as dioxane, acetone, tetrahydrofuran and the like.

The reaction may be illustrated as:

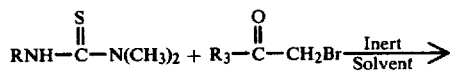

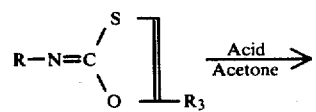

The substituted 2-imino-1,3-dithianes of the invention may be prepared according to the following general reaction:

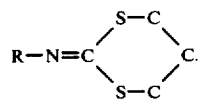

The preparation of the 1,3-dithietanes of the invention was carried out according to procedures known to those skilled in the art and described in U.S. Pat. Nos. 3,842,096, 3,928,382 and 3,954,801, herein incorporated by reference.

It will be recognized that the agriculturally acceptable salt of the above-described compounds is easily neutralized to form the free bases by the addition of a sufficient neutralizing amount of organic or inorganic base; contemplated, for example, are sodium hydroxide, potassium hydroxide, lithium bicarbonate, sodium bicarbonate, triethyl amine and sodium acetate.

To facilitate a further understanding of the present invention, the following illustrative examples are presented which are not to be taken as limitative of the invention.

EXAMPLE 1

2,3,3-Trichloroallyl N-(α-methylbenzyl) dithio carbamate

A two-phase mixture containing 6.0 g (0.0495 mol) dl-α-methylbenzylamine and 8.0 g (0.05 mol) 25% NaOH in 50 ml water was stirred rapidly at 0°–10° C. while 4.0 g (0.05 mol) carbon disulfide was added dropwise over 2–3 minutes. The mixture was stirred and allowed to warm to 20° C. over a one hour period. To this stirred slurry was added 9.0 g (0.05 mol) 1,1,2,3-tetrachloropropene in one portion. A yellow two phase mixture resulted and the temperature slowly rose to a maximum of 28° C. The mixture was heated gently to 45°–50° C. for three hours, then let cool and extracted with 300 ml ethyl ether. The ether solution was washed with two, 50 ml portions of water, treated with activated charcoal and $MgSO_4$, filtered through Hy-flo and evaporated in vacuo below 40°/<1 torr to give 14.9 g (88%) of a light orange oil.

Anal. Calc'd for $C_{12}H_{12}Cl_3NS_2$: N, 4.11; Cl, 31.2; S, 18.8; Found: N, 4.26; Cl, 31.4; S, 18.8.

EXAMPLE 2

Benzylamine, N-[4-(dichloromethylene)-1,3-dithiolan-2-ylidene] Hydrochloride

A solution containing 16.35 g (0.05 mol) of 2,3,3-trichloroallyl N-benzyldithiocarbamate in 50 ml of carbon tetrachloride was placed in a photochemical reaction vessel fitted with a fritted disc bottom for sparging $N_2$ through the solution. A 450-watt, Hanovia high pressure mercury lamp, with a Pyrex filter, was inserted into the water-cooled quartz immersion well. The solution was agitated with a gentle stream of $N_2$ bubbles and photolyzed for 35 minutes. The $CCl_4$ was decanted off leaving a solid which was triturated with benzene, collected by filtration and air dried to give 7.2 g mp 158°–161° C. A sample was recrystallized from $CHCl_3/CCl_4$ to give off-white crystals, mp 152°–159° C., yield 44%.

Anal. Calc'd for $C_{11}H_9Cl_2NS_2.HCl$: N, 4.29; Cl, 32.6; S, 19.6; N.E., 327; Found: N, 4.32; Cl, 32.4; S, 19.8; N.E., 321.

EXAMPLE 3

Benzylamine-,α-methyl-N-[(4-(dichloromethylene)-1,3-dithiolan-2-ylidene] Hydrochloride This compound was prepared according to the procedure described in Example 2 except that 2,3,3-trichloroallyl-N-α-methylbenzyl dithiocarbamate was used. A solid was obtained in 47.5% yield, mp 152°–153° C.

Anal. Calc'd for $C_{12}H_{11}Cl_2NS_2.HCl$: N, 4.11; Cl, 31.2; S, 18.8; Found: N, 4.06; Cl, 31.3; S, 19.0.

EXAMPLE 4

Benzylamine-,α-methyl-N-[4-(dichloromethylene)-1,3-dithiolan-2-ylidene]

A slurry consisting of 4.8 g (0.014 mol) of the hydrochloride salt of Example 3, in 60 ml of water was stirred and made slightly basic with triethylamine. The mixture was extracted with 50 ml ethyl ether. The separated ether solution was washed with 2, 25 ml portions of cold water, dried over $MgSO_4$ and evaporated in vacuo at 50°/<0.5 torr to give 4.1 g light amber oil. The oil which solidified on standing at room temperature was recrystallized from pet ether, mp 39°–40.5° C., yield 99%.

Anal. Calc'd for $C_{12}H_{11}Cl_2NS_2$: N, 4.60; Cl, 23.3; S, 21.1; Found: N, 4.71; Cl, 23.3; S, 21.1.

EXAMPLE 5

Benzylamine,α-isopropyl N-[4-(dichloromethylene)-1,3-dithiolan-2-ylidene]

A solution of 35.6 g (0.097 mol) 2,3,3-trichloroallyl N-(α-isopropyl) benzyldithiocarbamate in 100 ml chloroform was photolyzed for 2½–3 hours. After evaporation of the chloroform the residue was treated with benzene but no crystalline hydrochloride salt formed. The benzene solution was diluted with ethyl ether and the organic solution treated with dilute NaOH. The organic layer was then dried and evaporated to give 29.3 g red amber oil. A 10 g portion of this oil was purified by HPLC (High performance liquid chromatography) on silica gel using toluene to give 5.0 g of the pure free base, yield 45.7%.

Anal. Calc'd for $C_{14}H_{15}Cl_2NS_2$: N, 4.21; Cl, 21.3; S, 19.3; Found: N, 4.16; Cl, 21.4; S, 19.4.

EXAMPLE 6

Isopropylamine, N-[4-(dichloromethylene) 1,3-dithiolan-2-ylidene] Hydrochloride

A solution containing 10.0 g (0.036 mol) 2,3,3-trichloroallyl N-isopropyldithiocarbamate in 100 ml $CCl_4$ was photolyzed for 0.5 hour. The solid product was collected by filtration and air dried to give 3.8 g, mp 149°–154° C. Crystallization from $CHCl_3/CCl_4$ gave 2.5 g, mp 155°–157° C., yield 38%.

Anal. Calc'd for $C_7H_9Cl_2NS_2.HCl$: N, 5.03; Cl, 38.2; S, 23.0; Found: N, 5.05; Cl, 37.8; S, 22.8.

EXAMPLE 7

1,3-Dithiolane-,2-imino-4-dichloromethylene Hydrochloride

A solution containing 4.8 g (0.02 mol) 2,3,3-trichloroallyl dithiocarbamate in 75 mls of chloroform was photolyzed for one hour. The chloroform was drawn off through the bottom sintered glass frit and the solid residue triturated with fresh chloroform then air dried to give 3.3 g, mp 180° C. (dec.) sinters at 120° C. Crystallization from MeOH/ethyl ether gave a light tan powder, mp 187° C. (dec.).

Anal. Calc'd for $C_4H_3Cl_2NS_2.HCl$: N, 5.92; Cl, 45.0; S, 27.1; Found: N, 5.94; Cl, 44.2; S, 26.7.

Following the procedures described in Examples 2–7, other N-(4-dichloromethylene)-1,3-dithiolanes of the invention were prepared. Table I describes these compounds in greater detail.

TABLE I $$R-N=C\begin{matrix} S-CH_2 \\ | \\ S-C=CCl_2 \end{matrix}$$

| Example No. | Empirical | R | Analysis Calc'd | Found | Solvent | Mp °C. | % Yield |
|---|---|---|---|---|---|---|---|
| 8 | $C_5H_5Cl_2NS_2.HCl$ | $CH_3$— | N, 5.59; Cl, 42.4; S, 25.6; | 5.56 42.6 25.7 | $CCl_4$ | 193–194 | 46 |
| 9 | $C_{12}H_{10}Cl_3NS_2.HCl$ | 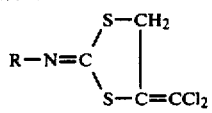 | N, 3.73; Cl 37.8; S, 17.1; | 3.78 37.7 17.1 | $CCl_4$ | 144–149 | 28.5 |

TABLE I-continued $$R-N=C\begin{smallmatrix}S-CH_2\\ \\S-C=CCl_2\end{smallmatrix}$$

| Example No. | Empirical | R | Analysis Calc'd | Found | Solvent | Mp °C | % Yield |
|---|---|---|---|---|---|---|---|
| 10 | $C_{13}H_{13}Cl_2NS_2 \cdot HCl$ | H₃C—⟨○⟩—CH(CH₃)— | N, 3.95; Cl, 30.0; S, 18.1; | 3.89 30.0 18.1 | CHCl₃ | 152.5–155.0 | 43 |
| 11 | $C_{16}H_{19}Cl_2NOS_2 \cdot HCl$ | H₃CO—⟨○⟩—CH(CH₃)— with H₃C-C(CH₃)₂ | N, 3.39; Cl, 25.8; S, 15.5; | 3.36 25.8 15.5 | CHCl₃ | 147–152.5 | 29.5 |
| 12 | $C_{13}H_{13}Cl_2NS_2$ | H₃C—⟨○⟩—CH(CH₃) | N, 4.40; Cl, 22.3; S, 20.1; | 4.43 22.4 20.1 | CHCl₃ | Oil | 94 |
| 13* | $C_{16}H_{19}Cl_2NS_2$ | ⟨○⟩—CH((CH₂)₄CH₃)— | N, 3.89; Cl, 19.7; S, 17.8; | 3.80 19.6 17.7 | CHCl₃ | Oil | 62 |

*Isolated by HPLC.

EXAMPLE 14

(After U.S. Pat. No. 3,449,365)

1,3-Dithiolan-2-imino-4-methylene-,Hydrochloride

To a flask immersed in an ice-water bath was added 14.7 g (0.12 mol) 2-propynyl dithiocarbamate and the solid then mixed with 14 ml concentrated hydrochloric acid. The initial solid mass was stirred with a thermometer and the mass slowly liquified whereupon the reaction became extremely exothermic and the temperature rose to 90° C. in spite of the ice-bath cooling. When the reaction had subsided and the temperature of the mixture had cooled to 25°–30° C., the reaction mass was poured into 250 ml acetone. Upon cooling and scratching, a sandy solid formed which was collected by a filtration, washed with fresh acetone and air dried to give 14.4 g, mp 119°–122° C. Recrystallization from Methanol/ether gave sandy crystals, mp 122°–123° C.

EXAMPLE 15

Benzylamine-α-methyl-N-[4-(methylene)-1,3-dithiolan-2-ylidene]

A slurry consisting of 18.2 g (0.15 mol) of dl-α-methylbenzylamine and 100 ml water containing 23.2 g (0.15 mol) 25.8% NaOH was stirred at 0°–10° C. while 11.4 g (0.15 mol) carbon disulfide was added over 10 minutes. The pink solution was stirred and slowly warmed to 25° C. over one hour whereupon 17.8 g (0.15 mol) propargyl bromide was added in one portion. An exothermic reaction caused the temperature to rise to 35° C. and a yellow oil precipitated. The mixture was stirred and heated to 50°–55° C. for five hours then cooled to 25° C. with stirring, overnight. The oil was extracted with 300 ml of ethyl ether and the separated ether solution washed with 100 water, dried over MgSO₄ and evaporated in vacuo to give 34.2 g red-orange oil. The nmr spectrum indicated a mixture of the propargyl ester and the cyclic 1,3-dithiolane. The oil was heated in vacuo at 70°–80° C. to complete the cyclization. The oil was dissolved in 300 ml ethyl ether and the ether solution extracted with three, 100 ml portions of 10% HCl, followed by two, 50 ml portions of water. The combined acid extract was extracted twice with 50 ml ether, then carefully neutralized with 10% NaOH and the precipitated oil taken up in ether. The ether solution was dried and evaporated at 55°/<1 torr to give 19.5 g (86.5%) light yellow oil, $n_D^{25}=1.6275$.

Anal. Calc'd for $C_{12}H_{13}NS_2$: C, 61.2; H, 5.57; N, 5.95; S, 27.2; Found: C, 61.5; H, 5.72; N, 6.04; S, 27.0.

EXAMPLE 16

Benzylamine,α-methyl, 2,5-dimethoxy-N-[4-(methylene)-1,3-dithiolan-2-ylidene]

A mixture of 10.0 g (0.034 mol) 2-propynyl N-[2,4-(dimethoxy)-α-methylbenzyl] dithiocarbamate and 30 ml conc. HCl was heated gently on a steam bath. After 10 minutes the solid carbamate had dissolved and the solution was heated an additional 10 minutes, cooled and ethyl ether added. The acid layer was separated, placed in an ice bath and carefully neutralized with 50% NaOH. The precipitated oil was extracted into ethyl ether and washed free of base with water, dried over MgSO₄ and evaporated in vacuo to give 9.7 g (97%) of a light amber oil, $n_D^{25}$ 1.6136.

Anal. Calc'd for $C_{14}H_{17}NO_2S_2$: C, 56.9; H, 5.80; N, 4.74; S, 21.7; Found: C, 57.1; H, 5.87; N, 4.70; S, 21.5.

EXAMPLE 17

Benzylamine-,α-methyl-N-[4-(methylene)-5-(methyl)-1,3-dithiolan-2-ylidene]

To a stirred solution containing 4.0 g (0.1 mol) NaOH and 10 ml of water in 100 ml dimethyl formamide there was added 2.1 g (0.1 mol) dl-α-methylbenzylamine at 20° C. followed by 7.6 g (0.1 mol) carbon disulfide over 5 minutes. After stirring for 15 minutes at 20°-25° C., 8.8 g (0.1 mol) of 3-chloro-1-butyne was added in portions. The resulting slurry was stirred at 20°-25° C. for one hour then heated gently to 30°-35° C. and stirred overnight at ambient temperature. The mixture was diluted with 400 ml cold water and extracted with 100 ml ethylene dichloride. The organic extract was washed with 50 ml water, dried over MgSO$_4$ and evaporated in vacuo below 30° C. to give 27.8 g orange oil which contained DMF. The oil was washed with water by decantation to remove DMF, then azeotroped with ethanol/benzene to give a crude oil which was dissolved in 300 ml ether and the solution extracted with 3 M HCl. The HCl extract was carefully neutralized with 25% NaOH and the precipitated oil extracted into ether, the solution dried and evaporated at 50°/<0.5 torr to give 9.0 g clear amber oil, yield 36% n$_D^{25}$ 1.6620.

Anal. Calc'd for C$_{12}$H$_{15}$NS$_2$: C, 62.6; H, 6.06; S, 25.7; Found: C, 62.7; H, 6.07; S, 25.6.

EXAMPLE 18

Benzeneethanamine, N-(4-methylene-1,3-dithiolan-2-ylidene)

A slurry containing 12.1 g (0.1 mol) β-phenethylamine and 15.4 g 25% sodium hydroxide in 100 ml water was stirred at 0°-10° C. while 7.7 g (0.1 mol) carbon disulfide was added dropwise. The orange solution was stirred rapidly and allowed to warm to room temperature over ~ one hour. Propargyl bromide, 13.4 g (0.113 mol) was then added slowly at 20°-25° C. (ice bath cooling) and the resulting slurry was stirred at room temperature overnight. The oily product was extracted into 50 ml of ethyl ether, the ether solution dried over MgSO$_4$ and evaporated in vacuo to give 21.6 g of an orange liquid. A 10 g sample of the crude oil was purified by HPLC on silica gel using toluene as eluant to yield 4.1 g (32%) n$_D^{25}$ 1.6020.

Anal. Calc'd for C$_{12}$H$_{13}$NS$_2$: C, 61.2; H, 5.57; N, 5.95; S, 27.3; Found: C, 61.1; H, 5.60; N, 5.92; S, 27.1.

EXAMPLE 19

Benzenepropaneamine, N-(4-methylene-1,3-dithiolan-2-ylidene)

A slurry containing 13.52 g (0.1 mol) of 3-phenyl-1-propylamine, 15.4 g (0.1 mol) 25% NaOH in 100 ml water was stirred vigorously at 0°-10° C. while 7.7 g (0.1 mol) carbon disulfide was added dropwise. The resulting solution was allowed to warm to ~25° C. over one hour whereupon 13.4 g (0.113 mol) propargyl bromide was added slowly at 20°-25° C. with ice bath cooling. The resulting two-phase mixture was stirred overnight then extracted with 50 ml ether. The ether solution was separated, washed until neutral with water, dried over MgSO$_4$ and evaporated in vacuo to give 22.7 g amber oil. After standing at room temperature for 8 days, 10 g of the crude oil was purified by HPLC on silica gel using toluene as eluant. Recovered 1.4 g (13%) of the pure 2-(3-phenyl-1-propyl)imino-4-methylene-1,3-dithiolane, n$_D^{25}$ 1.5983.

Anal. Calc'd for C$_{13}$H$_{15}$NS$_2$: C, 62.6; H, 6.06; N, 5.62; S, 25.7; Found: C, 62.4; H, 6.09; N, 5.58; S, 25.7.

The procedures of Examples 13-19 were used to prepare other N-(4-methylene)-1,3-dithiolanes which are described in Table II.

TABLE II

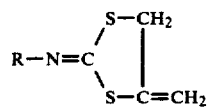

| Example No. | Empirical | R | Analysis Calc'd | Found | n$_D^{25°}$ | % Yield |
|---|---|---|---|---|---|---|
| 20 | C$_{11}$H$_{11}$NS$_2$ | ⌬—CH$_2$— | C, 59.7; H, 5.01; N, 6.33; S, 29.0; | 59.7 4.97 6.24 29.2 | 1.6489 | 66 |
| 21 | C$_7$H$_{11}$NS$_2$ | (CH$_3$)$_2$CH— | N, 8.08; S, 37.0; | 7.88 36.8 | 1.6041 | 88.5 |
| 22 | C$_{13}$H$_{15}$NS$_2$ | CH$_3$—⌬—CH(CH$_3$)— | C, 62.6; H, 6.06; N, 5.62; S, 25.7; | 62.7 6.09 5.59 25.7 | 1.6175 | 43 |
| 23 | C$_{14}$H$_{17}$NS$_2$ | CH$_3$CH$_2$—⌬—CH(CH$_3$)— | C, 63.9; H, 6.51; N, 5.32; S, 24.4; | 64.0 6.58 5.19 23.9 | 1.6083 | 60 |
| 24 | C$_{14}$H$_{17}$NS$_2$ | CH$_3$—⌬(CH$_3$)—CH(CH$_3$)— | C, 63.9; H, 6.51; N, 5.32; S, 24.4; | 64.2 6.61 5.20 23.7 | 1.6110 | 19 |

TABLE II-continued $$R-N=C\begin{matrix}S-CH_2\\S-C=CH_2\end{matrix}$$

| Example No. | Empirical | R | Analysis Calc'd | Found | $n_D^{25°}$ | % Yield |
|---|---|---|---|---|---|---|
| 25 | $C_{16}H_{21}NOS_2$ | 4-CH$_3$O-phenyl-CH(C(CH$_3$)$_3$)- | C, 62.5; H, 6.88; N, 4.56; S, 20.9; | 63.2; 6.96; 4.71; 20.2 | 1.5875 | 11 |
| 26* | $C_{16}H_{21}NS_2$ | phenyl-CH(-(CH$_2$)$_4$CH$_3$)- | C, 65.9; H, 7.26; N, 4.80; S, 22.0; | 66.3; 7.23; 4.70; 21.6 | 1.5856 | 55 |
| 27* | $C_{14}H_{17}NS_2$ | phenyl-CH(-CH(CH$_3$)$_2$)- | C, 63.9; H, 6.51; N, 5.32; S, 24.4; | 63.8; 6.52; 5.40; 24.3 | 1.5902 | 37 |
| 28* | $C_{12}H_{12}ClNS_2$ | 3-Cl-phenyl-CH(CH$_3$)- | C, 53.4; H, 4.48; Cl, 13.1; S, 23.8; | 53.5; 4.53; 13.2; 23.6 | 1.6154 | 27 |
| 29* | $C_{14}H_{17}NS_2$ | phenyl-CH(-(CH$_2$)$_2$CH$_3$)- | C, 63.9; H, 6.51; N, 5.32; S, 24.4; | 63.7; 6.58; 5.28; 24.3 | 1.6177 | 28 |
| 30* | $C_{13}H_{15}NS_2$ | phenyl-CH(C$_2$H$_5$)- | C, 62.6; H, 6.06; N, 5.62; S, 25.7; | 62.4; 6.06; 5.56; 25.6 | 1.5992 | 14 |
| 31* | $C_{15}H_{19}NS_2$ | phenyl-CH(-CH$_2$-CH(CH$_3$)$_2$)- | C, 64.9; H, 6.90; N, 5.05; S, 23.1; | 64.8; 6.88; 5.02; 23.0 | 1.5828 | 32 |
| 32* | $C_{15}H_{19}NS_2$ | phenyl-CH(-(CH$_2$)$_3$CH$_3$)- | C, 64.9; H, 6.90; N, 5.05; S, 23.1; | 64.8; 6.96; 4.98; 23.0 | 1.5960 | 32 |
| 33* | $C_{11}H_{10}ClNS_2$ | 2-Cl-phenyl-CH$_2$- | C, 51.6; H, 3.94; N, 5.48; Cl, 13.9; S, 25.1 | 51.7; 3.98; 5.47; 13.8; 25.0 | 1.6413 | 3 |

TABLE II-continued $$R-N=C\begin{smallmatrix}S-CH_2\\ \\S-C=CH_2\end{smallmatrix}$$

| Example No. | Empirical | R | Analysis Calc'd | Found | $n_D^{25°}$ | % Yield |
|---|---|---|---|---|---|---|
| 34* | $C_{11}H_{10}ClNS_2$ | 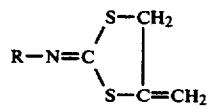 | C, 51.6; H, 3.94; N, 5.48; S, 25.1; | 51.4 3.99 5.46 25.0 | 1.6475 | 22 |

*Isolated by HPLC.

EXAMPLE 35

(After U.S. Pat. No. 3,449,366)

1,3-Dithiol-2-imino,4-methyl-,Hydrochloride

A mixture of 4.5 g (0.027 mol) 2-imino-4-methylene 1,3-dithiolane hydrochloride, Example 14, in 9 ml concentrated hydrochloric acid was heated at reflux in an oil bath (100°–110°) for three hours then allowed to cool and stand overnight at 25°–30° C. The dark solution was decanted away from a dark amorphous solid into 150 ml dry acetone. The light brown lustrous crystals which formed on standing in the cold were collected by a filtrate ion, washed with fresh acetone and air dried to give 3.5 g, mp 170°–173° C. Recrystallization from methanol gave bright yellow crystals which quickly darkened on air drying, mp 168°–170° C.

EXAMPLE 36

Benzylamine-,α-methyl-N-[4-(methyl)-1,3-dithiol-2-ylidene] Hydrochloride

A mixture containing 10.0 g (0.037 mol) 2-chloroallyl N-(α-methylbenzyl) dithiocarbamate, 14 ml conc. HCl and 25 ml ethanol was stirred and heated under reflux for 4 hours. The dark mixture was allowed to cool to 25° C. and poured into 200 ml acetone. Since no crystals formed on chilling, the solvent was evaporated in vacuo and the residue treated with 150 ml benzene and re-evaporated at 50°/<0.5 torr to give 10.4 g light yellow semi-solid which crystallized on treating with 100 ml ethyl ether and 5 ml methanol to yield 6.3 g cream solid, mp 139°–150° C. A sample was recrystallized from ether/methanol to give colorless crystals, mp 165°–166° C., yield 34%.

Anal. Calc'd for $C_{12}H_{13}NS_2.HCl$: N, 5.15; Cl, 13.0; S, 23.6, N.E. 272; Found: N, 5.27; Cl, 13.1; S, 23.7; N.E. 260.

EXAMPLE 37

Benzylamine-,α-t-butyl-p-methoxy-N-[4-(methyl)-1,3-dithiol-2-ylidene] Hydrochloride A mixture containing 24 g (0.07 mol) 2-chloroallyl N-[α-t-butyl-o-methoxybenzyl] dithiocarbamate and 40 ml conc. HCl in 70 ml ethanol was heated under reflux for 3 hours. The mixture was treated with 300 ml chloroform and the layers separated. The water layer was extracted with 3, 50 ml portions of CHCl₃ and the combined CHCl₃ extract was dried over MgSO₄ and evaporated to give a residue. The residue was dissolved in 25 ml methanol, treated with charcoal, filtered and slowly diluted with 3 liters of anhydrous ether. Upon stirring for 72 hours there was obtained 2.21 g white solids, mp 164°–167° C. The combination of the filtrate and washings from the above solids was evaporated to dryness and the residue again heated under reflux in 70 ml EtOH containing 40 ml conc. HCl. Chloroform extraction followed by treatment of the extract evaporation residue with methanol/ether as before, yielded 3.7 g solids, mp 161°–164° C., combined yield 21%.

Anal. Calc'd for $C_{16}H_{21}NOS_2.HCl$: N, 4.07; Cl, 10.31; S, 18.7; Found: N, 3.79; Cl, 9.45; S, 18.2.

EXAMPLE 38

Benzylamine,α-t-butyl-p-methoxy-N-[4-(methyl-1,3-dithiol-2-ylidene]

A stirred slurry, containing 2 g of the compound of Example 34, in 50 ml distilled water, was slowly neutralized with 25% NaOH with cooling. The mixture was treated with 50 ml ethyl ether, the ether layer was separated and was washed with water until neutral, dried over MgSO₄ and evaporated in vacuo to give 1.6 g colorless, viscous oil, yield 80%, $n_D^{25}$ 1.5851.

Anal. Calc'd for $C_{16}H_{21}NOS_2$: C, 62.5; H, 6.88; S, 20.9; Found: C, 62.8; H, 6.87; S, 20.5.

EXAMPLE 39

Benzeneethaneamine, N-(4-methyl-1,3-Dithiol-2-ylidene)

To a stirred slurry containing 12.12 g (0.1 mol) phenethylamine, 15.4 g (0.1 mol) 25% sodium hydroxide in 100 ml water was added 7.7 g (0.1 mol) carbon disulfide at 0°–10° C. over ~5 minutes. To the resulting solution was added 12.2 g (0.11 mol) 2,3-dichloropropene at 20°–25° C. and the mixture allowed to stir overnight at 25°–30° C. The two-phase mixture was extracted with 50 ml of ether, the ether solution separated, dried over MgSO₄ and evaporated in vacuo to give 20.3 g amber oil. The oil was dissolved in 70 ml ethanol, 40 ml conc. HCl added and the mixture heated under reflux for six hours. After cooling and standing overnight the mixture was vacuum treated to remove the ethanol and excess HCl and the residue treated with benzene three times to azeotrope the water. The resulting residue was treated with ethyl ether, stirred two hours and filtered to yield 11.0 g light tan crystals, mp 80°–106° C. The crude salt, (10 g) was dissolved in 50 ml water, neutralized with 25% NaOH and the free base taken up in ether. The ether solution was washed until neutral, dried and evaporated to give 7.8 g amber oil which was purified by HPLC on silica gel using toluene as eluant. There was obtained 6.0 g, $n_D^{25}$ 1.5990, yield 40%.

Anal. Calc'd for $C_{12}H_{13}NS_2$: C, 61.2; H, 5.57; N, 5.95; S, 27.3; Found: C, 61.4; H, 5.60; N, 5.90; S, 27.1.

Table III describes other compounds of the invention prepared in accordance with the procedure described in Examples 33–39.

EXAMPLE 49

Benzylamine-α-methyl-N-[5-(phenyl)-1,3-oxathiol-2-ylidene]

A stirred solution containing 10.0 g (0.048 mol) of 1-(α-methyl)benzyl-3,3-dimethylthiourea and 10.0 g (0.05 mol) of 97% α-bromoacetophenone in 100 ml

TABLE III $$R-N=C\begin{array}{c}S-CH\\ \| \\ S-C-CH_3\end{array}$$

| Example No. | Empirical | R | Analysis Calc'd | Found | Mp °C./$n_D^{25}$ | % Yield |
|---|---|---|---|---|---|---|
| 40 | $C_{14}H_{17}NS_2 \cdot HCl$ | (CH(CH₃)₂)-C₆H₄-CH- | C, 56.1; H, 6.05; N, 4.67; S, 21.4 | 56.1; 6.06; 4.65; 21.3 | 160–163 | 33 |
| 41 | $C_{16}H_{21}NS_2 \cdot HCl$ | (CH₃)(CH₂)₄-C₆H₄-CH- | N, 4.27; Cl, 19.5; S, 10.8 | 4.11; 19.3; 10.7 | 150–152 | 16 |
| 42 | $C_{13}H_{15}NS_2 \cdot HCl$ | C₆H₅-CH(CH₃)- | C, 54.6; H, 5.64; N, 4.90; S, 22.4 | 54.7; 5.67; 4.96; 22.3 | 161–164 | 5 |
| 43* | $C_{13}H_{15}NS_2$ | C₆H₅-CH(C₂H₅)- | C, 62.6; H, 6.06; N, 5.62; S, 25.7 | 62.5; 6.07; 5.64; 25.7 | 1.5973 | 14 |
| 44* | $C_{13}H_{15}NS_2$ | C₆H₅-CH₂CH₂CH₂- | C, 62.6; H, 6.06; N, 5.62; S, 25.7 | 62.5; 6.10; 5.62; 25.6 | 1.5892 | 8 |
| *45 | $C_{11}H_{10}ClNS_2$ | 2-Cl-C₆H₄-CH₂- | C, 51.6; H, 3.94; N, 5.48 | 51.8; 3.95; 5.51 | 1.6266 | 13 |
| 46* | $C_{11}H_{10}ClNS_2$ | 2-Cl-C₆H₄-CH₂- | C, 51.6; H, 3.94; N, 5.48; S, 25.1 | 51.8; 4.00; 5.51; 25.0 | 55–60° | 5 |
| 47 | $C_{14}H_{17}NS_2$ | (CH(CH₃)₂)-C₆H₄-CH- | C, 63.8; H, 6.51; S, 24.3 | 63.7; 6.54; 24.2 | 1.5828 | 8 |
| 48* | $C_{12}H_{12}ClNS_2$ | 2-Cl-C₆H₄-CH(CH₃)- | N, 5.19; Cl, 13.1; S, 23.8 | 5.19; 13.3; 23.7 | 1.6083 | 27 |

*Isolated by HPLC dioxane was heated under reflux for 17 hours. The hot mixture was filtered, the filtrate was allowed to cool and then filtered again to remove a small amount of hygroscopic solids. Evaporation of the filtrate gave 15.2 g dark amber viscous oil which was taken up in ethyl ether and the solution washed with water until neutral, dried and evaporated to give 10.9 g dark brown oil which was purified by chromatography on silica gel using pet. ether/benzene yielding 3.5 g (12.5%) mp 67°–70° C. A sample was crystallized from pentane, mp 70°–72° C.

Anal. Calc'd for $C_{17}H_{15}NOS$: C, 72.6; H, 5.37; N, 4.98; S, 11.4; Found: C, 72.6; H, 5.37; N, 4.95; S, 11.4.

EXAMPLE 50

5-Benzeneamine, N-(5-phenyl-1,3-oxathiol-2-ylidene)

This compound was prepared according to the procedure described in Example 49 except that 1-phenyl-3,3-dimethylthiourea was used; the final product melted at 135°–136° C.

EXAMPLE 51

Benzylamine-N-(1,3-dithian-2-ylidene)

To a stirred solution of 10.7 g (0.1 mol) benzylamine in 100 ml DMF there was added 20 ml 10 N KOH at 25°–30° C. with ice bath cooling, followed by the addition of 7.6 g (0.1 mol) carbon disulfide. The resulting yellow solution was stirred at 25°–30° C. for one-half hour. 1,3-dibromopropane, 20.2 g (0.1 mol), was added dropwise to the above solution causing the temperature to rise slowly to 38° C. with precipitation of white solids. The mixture was stirred for 2.5 hours, chilled in an ice bath and filtered to give 19.7 g. The solid was treated with chloroform and water and the organic layer dried over $MgSO_4$ and solvent evaporated to yield 3.3 g, 10% yield, mp 125°–127.5° C.

Anal. Calc'd for $C_{11}H_{13}NS_2$: C, 59.2; H, 5.87; S, 28.7; Found: C, 59.1; H, 5.88; S, 28.7.

EXAMPLE 52 o-Toluidine, 4-chloro-N-(1,3-dithietan-2-ylidene)-Hydrochloride o-Toluidine, 4-chloro-N-(1,3-dithietan-2-ylidene) was prepared according to the procedure described in U.S. Pat. No. 3,954,801, mp 165.5°–169° C.

Anal. Calc'd for $C_9H_8ClNS_2 \cdot HCl$: N, 5.27; Cl, 26.6; S, 24.1; Found: C, 5.37; Cl, 26.5; S, 23.8.

EXAMPLE 53 o-Toluidine, 4-chloro-, N-(1,3-dithietan-2-ylidene)

o-Toluidine, 4-chloro-, N-(1,3-dithietan-2-ylidene) was prepared by neutralizing an aqueous solution of the compound of Example 52 with 25% NaOH. An off-white solid was recovered which melted at 41°–44° C.

Anal. Calc'd for $C_9H_8ClNS_2$: N, 6.10, Cl, 15.4; S, 27.9; Found: N, 6.19; Cl, 15.5; S, 27.4.

The following examples are presented to illustrate the safening effectiveness of the compounds of the present invention as well as the various embodiments of the invention. These examples are presented as being illustrative of the novel usages of the invention and are not intended to be a limitation as to the scope thereof.

EXAMPLE 54

Aluminum pans or plastic pots are filled with prepared Ray silt loam soil and compacted to a depth of ½ inch from the top of the container. The pans or pots are then planted with seeds or vegetative propagules of the desired plant species. Soil cover layers, of prepared Ray silt loam, are sequentially treated with antidote and herbicide. The antidote, dissolved in a suitable solvent, is applied to the soil cover layer followed by herbicide application. The desired concentration of herbicide is formulated as a solution, emulsifiable concentrate or wettable powder in a suitable solvent. After antidote and herbicide are applied to the soil cover layer, the combination is thoroughly incorporated into the soil cover layer by stirring or shaking. The soil cover layers are then placed on the pre-seeded pans or pots and the pans or pots are transferred to a greenhouse bench where they are watered from below. Two to four weeks after application of the antidote and herbicide combination, the results are observed and recorded. Pans or pots treated only with antidote or herbicide are prepared and treated as described above. The results observed from the pans or pots provide the measure of plant inhibition due to antidote and herbicide alone. The "safening effect" of the antidote is calculated as follows: [% Plant Inhibition due to Herbicide + % Plant Inhibition due to Antidote − % Plant Inhibition due to Antidote/Herbicide Combination].

Table IV summarizes the results obtained when the compounds of the invention were tested in accordance with the procedure of Example 54 utilizing triallate as the herbicide.

TABLE IV

| Compound of Example No. | Rate of Triallate (lb/A) | Rate of Antidote (lb/A) | Safening Effect | | |
|---|---|---|---|---|---|
| | | | Rice | Sorghum | Wheat |
| 3 | 0.25 | 8.0 | 70 | 85 | 85 |
| 15 | 0.375 | 8.0 | 34 | 70 | 33 |
| 4 | 0.25 | 8.0 | 65 | 70 | 75 |
| 14 | 0.25 | 4.0 | * | * | * |
| 14 | 0.375 | 8.0 | * | * | 38 |
| 35 | 0.25 | 4.0 | 40 | * | 25 |
| 35 | 0.375 | 8.0 | * | * | * |
| 36 | 0.25 | 8.0 | 65 | 75 | 45 |
| 7 | 0.375 | 8.0 | * | * | * |
| 2 | 0.375 | 8.0 | * | 55 | 28 |
| 20 | 0.375 | 8.0 | 34 | 90 | 33 |
| 21 | 0.375 | 8.0 | 20 | 70 | 43 |
| 6 | 0.375 | 8.0 | * | 83 | 30 |
| 52 | 0.375 | 8.0 | 40 | 93 | 40 |
| 53 | 0.375 | 8.0 | * | 93 | 25 |
| 8 | 0.5 | 8.0 | * | 48 | 20 |
| 17 | 0.5 | 8.0 | 35 | 85 | 30 |
| 50 | 0.5 | 8.0 | * | * | * |
| 49 | 0.5 | 8.0 | 65 | 78 | 55 |
| 9 | 0.5 | 8.0 | * | * | 20 |
| 22 | 0.5 | 8.0 | 55 | 87 | 50 |
| 10 | 0.5 | 8.0 | * | 22 | 70 |
| 23 | 0.5 | 8.0 | 25 | 97 | 50 |
| 24 | 0.5 | 8.0 | 25 | 90 | 25 |
| 25 | 0.5 | 8.0 | 20 | 65 | * |
| 11 | 0.5 | 8.0 | * | 63 | * |
| 16 | 0.5 | 8.0 | * | 38 | * |
| 12 | 0.5 | 8.0 | 20 | 30 | 80 |
| 40 | 0.5 | 8.0 | 20 | 79 | 48 |
| 5 | 0.5 | 8.0 | 23 | 45 | * |
| 13 | 0.5 | 8.0 | * | * | * |
| 41 | 0.5 | 8.0 | * | 55 | * |
| 26 | 0.5 | 8.0 | 30 | * | * |
| 37 | 0.5 | 8.0 | * | 30 | * |
| 38 | 0.5 | 8.0 | * | * | * |
| 42 | 0.5 | 8.0 | 20 | * | 43 |
| 47 | 0.5 | 8.0 | * | * | * |
| 27 | 0.5 | 8.0 | 90 | 85 | 65 |
| 48 | 0.5 | 8.0 | — | 82 | 84 |
| 48 | 0.5 | 8.0 | * | 80 | * |
| 28 | 0.5 | 8.0 | * | 58 | * |
| 43 | 0.5 | 8.0 | * | 30 | 28 |
| 29 | 0.5 | 8.0 | 40 | * | * |

TABLE IV-continued

| Compound of Example No. | Rate of Triallate (lb/A) | Rate of Antidote (lb/A) | Safening Effect | | |
|---|---|---|---|---|---|
| | | | Rice | Sorghum | Wheat |
| 30 | 0.5 | 8.0 | * | 20 | 60 |
| 18 | 0.5 | 8.0 | 21 | 82 | 16 |
| 31 | 0.5 | 8.0 | * | * | * |
| 32 | 0.5 | 8.0 | 50 | * | * |
| 39 | 0.5 | 8.0 | * | * | * |
| 19 | 0.5 | 8.0 | * | 48 | * |
| 44 | 0.5 | 8.0 | * | 68 | * |
| 33 | 0.5 | 8.0 | * | 67 | 35 |
| 34 | 0.5 | 8.0 | * | * | * |
| 45 | 0.5 | 8.0 | * | 40 | * |
| 46 | 0.5 | 8.0 | * | * | * |
| 51 | 0.5 | 8.0 | 50 | 90 | * |
| 21 | 0.125 | 8.0 | 20 | 35 | 28 |
| | 0.25 | 8.0 | * | 75 | 50 |
| | 0.5 | 8.0 | * | 47 | 34 |
| | 1.0 | 8.0 | * | * | * |
| 52 | 0.125 | 8.0 | * | 88 | 20 |
| | 0.25 | 8.0 | 30 | 77 | * |
| | 0.5 | 8.0 | 33 | 22 | * |
| | 1.0 | 8.0 | * | * | * |
| 49 | 0.125 | 8.0 | * | * | 20 |
| | 0.25 | 8.0 | 45 | 40 | 60 |
| | 0.5 | 8.0 | 53 | 60 | 58 |
| | 1.0 | 8.0 | 24 | 68 | 25 |
| 30 | 0.25 | 8.0 | 25 | 65 | 50 |
| | 0.5 | 8.0 | 20 | * | * |
| | 1.0 | 8.0 | * | * | * |
| | 2.0 | 8.0 | * | * | * |
| 27 | 0.25 | 8.0 | 30 | 84 | 70 |
| | 0.50 | 8.0 | 55 | 50 | 87 |
| | 1.0 | 8.0 | 66 | 50 | 28 |
| | 2.0 | 8.0 | 55 | 20 | * |

*Safening effect was between 0 and 19

Following the procedure of Example 54, the compounds of the invention were tested on rice, sorghum and wheat utilizing the acetanilide herbicide alachlor. The results are summarized in Table V.

TABLE V

| Compound of Example No. | Rate of Alachlor (lb/A) | Rate of Antidote (lb/A) | Safening Effect | | |
|---|---|---|---|---|---|
| | | | Rice | Sorghum | Wheat |
| 3 | 1.0 | 8.0 | 35 | 20 | * |
| 15 | 2.0 | 8.0 | * | 42 | 40 |
| 4 | 1.0 | 8.0 | 25 | * | * |
| 14 | 2.0 | 8.0 | 93 | * | * |
| 14 | 2.0 | 4.0 | * | * | * |
| 35 | 2.0 | 8.0 | 43 | * | * |
| 35 | 2.0 | 4.0 | 28 | * | * |
| 36 | 2.0 | 8.0 | 78 | 45 | 43 |
| 7 | 2.0 | 8.0 | * | * | * |
| 2 | 2.0 | 8.0 | * | * | * |
| 20 | 2.0 | 8.0 | * | 70 | 40 |
| 21 | 2.0 | 8.0 | * | * | * |
| 6 | 2.0 | 8.0 | 33 | * | * |
| 52 | 2.0 | 8.0 | * | * | * |
| 53 | 2.0 | 8.0 | 48 | 20 | * |
| 8 | 2.0 | 8.0 | 28 | * | 23 |
| 17 | 2.0 | 8.0 | * | 35 | 25 |
| 50 | 2.0 | 8.0 | * | * | * |
| 49 | 4.0 | 8.0 | * | * | 20 |
| 9 | 4.0 | 8.0 | * | * | * |
| 22 | 4.0 | 8.0 | * | 25 | * |
| 10 | 4.0 | 8.0 | * | * | * |
| 23 | 4.0 | 8.0 | * | 25 | 20 |
| 24 | 4.0 | 8.0 | * | * | * |
| 25 | 4.0 | 8.0 | * | * | * |
| 11 | 4.0 | 8.0 | * | * | * |
| 16 | 4.0 | 8.0 | * | * | * |
| 12 | 4.0 | 8.0 | * | * | * |
| 40 | 4.0 | 8.0 | * | * | * |
| 5 | 4.0 | 8.0 | 35 | * | * |
| 13 | 4.0 | 8.0 | * | * | * |
| 41 | 4.0 | 8.0 | * | * | * |
| 26 | 4.0 | 8.0 | * | * | * |

TABLE V-continued

| Compound of Example No. | Rate of Alachlor (lb/A) | Rate of Antidote (lb/A) | Safening Effect | | |
|---|---|---|---|---|---|
| | | | Rice | Sorghum | Wheat |
| 37 | 4.0 | 8.0 | * | * | * |
| 38 | 4.0 | 8.0 | * | * | 20 |
| 42 | 4.0 | 8.0 | * | * | * |
| 47 | 4.0 | 8.0 | * | * | * |
| 27 | 4.0 | 8.0 | * | * | * |
| 48 | 2.0 | 8.0 | * | * | * |
| 48 | 4.0 | 8.0 | — | * | * |
| 28 | 2.0 | 8.0 | * | 43 | * |
| 29 | 2.0 | 8.0 | * | * | * |
| 43 | 2.0 | 8.0 | * | 20 | * |
| 30 | 2.0 | 8.0 | 31 | * | * |
| 18 | 2.0 | 8.0 | * | * | * |
| 31 | 2.0 | 8.0 | * | * | * |
| 32 | 2.0 | 8.0 | * | * | * |
| 39 | 2.0 | 8.0 | * | * | 25 |
| 19 | 2.0 | 8.0 | 40 | * | * |
| 44 | 2.0 | 8.0 | * | * | * |
| 33 | 2.0 | 8.0 | 20 | * | * |
| 34 | 2.0 | 8.0 | * | * | * |
| 45 | 4.0 | 8.0 | * | 20 | * |
| 46 | 4.0 | 8.0 | * | * | * |
| 51 | 4.0 | 8.0 | * | * | * |
| 3 | 0.5 | 8.0 | | 55 | |
| | 1.0 | 8.0 | | 50 | |
| | 2.0 | 8.0 | | 20 | |
| | 4.0 | 8.0 | | 40 | |
| 36 | 0.5 | 8.0 | | 35 | |
| | 1.0 | 8.0 | | 50 | |
| | 2.0 | 8.0 | | 63 | |
| | 4.0 | 8.0 | | 64 | |
| 20 | 0.5 | 8.0 | | 78 | |
| | 1.0 | 8.0 | | 64 | |
| | 2.0 | 8.0 | | 34 | |
| | 4.0 | 8.0 | | 20 | |
| 17 | 0.0625 | 8.0 | | * | |
| | 0.25 | 8.0 | | 43 | |
| | 1.0 | 8.0 | | 54 | |
| | 4.0 | 8.0 | | * | |
| 22 | 0.5 | 8.0 | | 65 | |
| | 1.0 | 8.0 | | 63 | |
| | 2.0 | 8.0 | | 77 | |
| | 4.0 | 8.0 | | * | |
| 23 | 0.5 | 8.0 | | 70 | |
| | 1.0 | 8.0 | | 48 | |
| | 2.0 | 8.0 | | 22 | |
| | 4.0 | 8.0 | | * | |
| 28 | 0.5 | 8.0 | | 40 | |
| | 1.0 | 8.0 | | 26 | |
| | 2.0 | 8.0 | | * | |
| | 4.0 | 8.0 | | * | |
| 43 | 0.5 | 8.0 | | * | |
| | 1.0 | 8.0 | | 40 | |
| | 2.0 | 8.0 | | 20 | |
| | 4.0 | 8.0 | | 40 | |

*Safening effect was between 0 and 19

Utilizing the procedure of Example 54, the compounds of the invention were tested on rice, sorghum and wheat against the acetanilide herbicide butachlor. The results are summarized in Table VI.

TABLE VI

| Compound of Example No. | Rate of Butachlor (lb/A) | Rate of Antidote (lb/A) | Safening Effect | | |
|---|---|---|---|---|---|
| | | | Rice | Sorghum | Wheat |
| 3 | 4.0 | 8.0 | 30 | 35 | 20 |
| 15 | 4.0 | 8.0 | 20 | 58 | 38 |
| 4 | 4.0 | 8.0 | 35 | 35 | * |
| 14 | 4.0 | 8.0 | * | * | * |
| 14 | 4.0 | 8.0 | * | * | * |
| 35 | 4.0 | 8.0 | 23 | * | 23 |
| 35 | 4.0 | 8.0 | 25 | * | * |
| 36 | 4.0 | 8.0 | 68 | 28 | 40 |
| 7 | 4.0 | 8.0 | * | 25 | * |
| 2 | 4.0 | 8.0 | 35 | * | 23 |
| 20 | 4.0 | 8.0 | 55 | 40 | 53 |

TABLE VI-continued

| Compound of Example No. | Rate of Butachlor (lb/A) | Rate of Antidote (lb/A) | Safening Effect | | |
|---|---|---|---|---|---|
| | | | Rice | Sorghum | Wheat |
| 21 | 4.0 | 8.0 | 20 | 25 | * |
| 6 | 4.0 | 8.0 | * | 53 | * |
| 52 | 4.0 | 8.0 | * | * | * |
| 53 | 4.0 | 8.0 | 20 | * | 38 |
| 8 | 4.0 | 8.0 | * | * | 30 |
| 17 | 4.0 | 8.0 | 73 | 50 | 25 |
| 50 | 4.0 | 8.0 | * | 30 | * |
| 49 | 4.0 | 8.0 | * | 38 | * |
| 9 | 4.0 | 8.0 | * | 30 | 20 |
| 22 | 4.0 | 8.0 | * | 55 | 38 |
| 10 | 4.0 | 8.0 | * | * | * |
| 23 | 4.0 | 8.0 | * | 60 | * |
| 24 | 4.0 | 8.0 | 20 | 60 | 45 |
| 25 | 4.0 | 8.0 | * | * | * |
| 11 | 4.0 | 8.0 | * | 58 | * |
| 16 | 4.0 | 8.0 | * | * | 60 |
| 12 | 4.0 | 8.0 | * | 35 | * |
| 40 | 4.0 | 8.0 | * | 30 | * |
| 5 | 4.0 | 8.0 | 55 | * | 28 |
| 13 | 4.0 | 8.0 | 20 | * | * |
| 41 | 4.0 | 8.0 | * | * | * |
| 26 | 4.0 | 8.0 | * | 23 | * |
| 37 | 4.0 | 8.0 | 20 | * | * |
| 38 | 4.0 | 8.0 | * | * | * |
| 42 | 4.0 | 8.0 | 25 | * | 48 |
| 47 | 4.0 | 8.0 | * | * | 33 |
| 27 | 4.0 | 8.0 | 33 | * | * |
| 48 | 4.0 | 8.0 | * | 25 | 20 |
| 48 | 4.0 | 8.0 | — | * | 35 |
| 28 | 4.0 | 8.0 | * | * | 35 |
| 29 | 4.0 | 8.0 | * | * | * |
| 43 | 4.0 | 8.0 | 38 | 32 | 25 |
| 30 | 4.0 | 8.0 | 25 | * | 33 |
| 18 | 4.0 | 8.0 | 34 | * | 35 |
| 31 | 4.0 | 8.0 | 39 | * | * |
| 32 | 4.0 | 8.0 | 20 | 30 | 20 |
| 39 | 4.0 | 8.0 | * | * | * |
| 19 | 4.0 | 8.0 | * | * | * |
| 44 | 4.0 | 8.0 | 25 | * | * |
| 33 | 4.0 | 8.0 | 55 | * | 20 |
| 34 | 6.0 | 8.0 | * | * | 25 |
| 45 | 6.0 | 8.0 | 25 | * | * |
| 46 | 6.0 | 8.0 | 68 | 23 | * |
| 51 | 6.0 | 8.0 | 35 | * | 40 |

*Safening effect was between 0 and 19

The antidotes of the present invention may also be applied to the crop seed prior to planting. This is often a desirable mode of application as relatively small amounts of antidote are used compared to preemergence soil incorporation of antidote. The following examples describe the use of the antidote compounds of the present invention as seed treatments in greater detail.

EXAMPLE 55

Toluene solutions or suspensions of antidote are applied to the crop seed at the desired seed treatment concentration. Untreated (control) and treated seeds were planted in 9½×5¼×2¾ inch deep pans containing Ray silt loam soil. Soil cover layers (450 gm) were sprayed with the desired concentration of herbicide using a belt sprayer (20 gpa), incorporated and placed on pre-seeded pans. The pans were given ¼ inch of overhead water and transferred to greenhouse benches. The pans were sub-irrigated as required during the remainder of the test. Observations were made 2½ to 3 weeks after treatment and the results recorded. The amount of antidote applied to the crop seed is calculated on % w/w basis defined as 1 part of antidote per 1000 parts of crop seed. The observations made and recorded in accordance with the above procedure utilizing triallate as the herbicide are shown in Table VII.

The results summarized in Table VII are shown as % Inhibition for untreated and teated seeds at varying rates of triallate herbicide and antidote. A—indicates that a reduction in expected inhibition occurred. That is, if "safening effect" were calculated, 20 units or greater "safening" occurred. The protection or "safening" afforded the crop plant by treatment of the crop seed with the "antidotal" compounds of the invention may be calculated as follows:

% Inhibition of Crop Plant (No Seed Treatment) —
% Inhibition of Crop Plant (Seed Treatment).

TABLE VII

| Triallate Rate Lb/A | Seed Treatment Compound of Example No. | Crop | % Crop Inhibition* Seed Treatment Conc., % W/W | | | | | |
|---|---|---|---|---|---|---|---|---|
| | | | 0 | 1/6 | 1/8 | 1/4 | 1/2 | 1 |
| 0 | 3 | Wheat | 0 | 0 | 0 | 10 | 0 | 3 |
| 1/16 | 3 | Wheat | 10 | 5 | 0 | 5 | 0 | 0 |
| 1/8 | 3 | Wheat | 53 | 0— | 0— | 0— | 0— | 0— |
| 1/4 | 3 | Wheat | 88 | 0— | 0— | 0— | 0— | 5— |
| 1/2 | 3 | Wheat | 99 | 5— | 10— | 10— | 0— | 13— |
| 1 | 3 | Wheat | 100 | 10— | 0— | 0— | 5— | 8— |
| 2 | 3 | Wheat | 100 | 48— | 35— | 20— | 25— | 15— |
| | | | 0 | 1/2 | 1 | 2 | 4 | |
| 0 | 3 | Wheat | 0 | 0 | 0 | 10 | 18 | |
| 1/16 | 3 | Wheat | 0 | 0 | 0 | 23 | 13 | |
| 1/8 | 3 | Wheat | 23 | 0— | 0— | 8— | 23 | |
| 1/4 | 3 | Wheat | 70 | 0— | 0— | 5— | 20— | |
| 1/2 | 3 | Wheat | 99 | 0— | 0— | 8— | 18— | |
| 1 | 3 | Wheat | 99 | 0— | 0— | 20— | 8— | |
| 2 | 3 | Wheat | 100 | 0— | 10— | 13— | 15— | |
| 4 | 3 | Wheat | 100 | 30— | 58— | 20— | 30— | |
| 0 | 4 | Wheat | 0 | 0 | 5 | 25 | 28 | |
| 1/16 | 4 | Wheat | 5 | 0 | 10 | 23 | 23 | |
| 1/8 | 4 | Wheat | 28 | 20 | 0— | 23— | 25— | |
| 1/4 | 4 | Wheat | 65 | 0— | 3— | 20— | 40— | |
| 1/2 | 4 | Wheat | 93 | 0— | 0— | 30— | 15— | |
| 1 | 4 | Wheat | 95 | 0— | 5— | 28— | 30— | |
| 2 | 4 | Wheat | 98 | 0— | 10— | 38— | 35— | |
| 4 | 4 | Wheat | 100 | 23— | 20— | 40— | 48— | |
| | | | 0 | 1/32 | 1/8 | 1/2 | | |
| 0 | 3 | Wheat | 0 | 0 | 0 | 0 | | |
| 1/16 | 3 | Wheat | 5 | 5 | 0 | 5 | | |
| 1/8 | 3 | Wheat | 28 | 0— | 0— | 0— | | |
| 1/4 | 3 | Wheat | 60 | 0— | 0— | 0— | | |
| 1/2 | 3 | Wheat | 88 | 8— | 0— | 0— | | |
| 1 | 3 | Wheat | 99 | 20— | 8— | 10— | | |
| 2 | 3 | Wheat | 100 | 78— | 55— | 63— | | |
| 0 | 15 | Wheat | 0 | 0 | 0 | 10 | | |
| 1/16 | 15 | Wheat | 10 | 0 | 0 | 15 | | |
| 1/8 | 15 | Wheat | 40 | 10 | 5— | 20— | | |
| 1/4 | 15 | Wheat | 65 | 40 | 10— | 40— | | |
| 1/2 | 15 | Wheat | 95 | 60 | 20— | 40— | | |
| 1 | 15 | Wheat | 98 | 80 | 55— | 45— | | |
| 2 | 15 | Wheat | 99 | 95 | 65— | 55— | | |
| 0 | 4 | Wheat | 0 | 0 | 0 | 0 | | |
| 1/16 | 4 | Wheat | 5 | 0 | 0 | 5 | | |
| 1/8 | 4 | Wheat | 18 | 5 | 0 | 0 | | |
| 1/4 | 4 | Wheat | 70 | 0— | 0— | 0— | | |
| 1/2 | 4 | Wheat | 98 | 5— | 0— | 0— | | |
| 1 | 4 | Wheat | 99 | 35— | 13— | 20— | | |
| 2 | 4 | Wheat | 99 | 80 | 40— | 25— | | |
| | | | 0 | 1/16 | 1/4 | 1 | | |
| 0 | 3 | Oats | 0 | 0 | 0 | 0 | | |
| 1/128 | 3 | Oats | 0 | 0 | 0 | 0 | | |
| 1/64 | 3 | Oats | 40 | 8— | 3— | 3— | | |
| 1/32 | 3 | Oats | 65 | 5— | 8— | 23— | | |
| 1/16 | 3 | Oats | 93 | 60— | 60— | 53— | | |
| 1/8 | 3 | Oats | 95 | 88 | 75— | 80 | | |
| 1/4 | 3 | Oats | 100 | 99 | 86 | 98 | | |
| 0 | 4 | Oats | 0 | 0 | 5 | 3 | | |
| 1/128 | 4 | Oats | 0 | 0 | 0 | 0 | | |
| 1/64 | 4 | Oats | 28 | 5— | 20— | 5— | | |
| 1/32 | 4 | Oats | 88 | 5— | 0— | 3— | | |

TABLE VII-continued

| Triallate Rate Lb/A | Seed Treatment Compound of Example No. | Crop | % Crop Inhibition* Seed Treatment Conc., % W/W | | | |
|---|---|---|---|---|---|---|
| | | | 0 | 1/8 | 1/4 | |
| 1/16 | 4 | Oats | 98 | 25— | 28— | 40— |
| 1/8 | 4 | Oats | 100 | 99 | 80— | 73— |
| 1/4 | 4 | Oats | 100 | 100 | 92 | 90 |
| 0 | 3 | Barley | 0 | 0 | 0 | 0 |
| 1/8 | 3 | Barley | 0 | 0 | 0 | 0 |
| 1/4 | 3 | Barley | 15 | 0 | 0 | 0 |
| 1/2 | 3 | Barley | 78 | 28— | 3— | 8— |
| 1 | 3 | Barley | 95 | 83 | 25— | 35— |
| 2 | 3 | Barley | 100 | 95 | 70— | 35— |
| 4 | 3 | Barley | 100 | 99 | 93 | 68— |
| 0 | 4 | Barley | 0 | 0 | 0 | 0 |
| 1/8 | 4 | Barley | 0 | 0 | 0 | 0 |
| 1/4 | 4 | Barley | 15 | 0 | 0 | 0 |
| 1/2 | 4 | Barley | 75 | 18— | 3— | 3— |
| 1 | 4 | Barley | 90 | 30— | 5— | 10— |
| 2 | 4 | Barley | 99 | 83 | 53— | 68— |
| 4 | 4 | Barley | 100 | 100 | 90 | 78 |
| | | | 0 | 1/8 | 1/4 | |
| 0 | 3 | Wheat | 0 | 0 | 0 | |
| 1/16 | 3 | Wheat | 0 | 0 | 0 | |
| 1/8 | 3 | Wheat | 28 | 0— | 10— | |
| 1/4 | 3 | Wheat | 53 | 0— | 0— | |
| 1/2 | 3 | Wheat | 92 | 0— | 8— | |
| 1 | 3 | Wheat | 100 | 0— | 8— | |
| 2 | 3 | Wheat | 100 | 53— | 15— | |
| 4 | 3 | Wheat | 100 | 68— | 78— | |
| 0 | 3 | Barley | 0 | 0 | 0 | |
| 1/16 | 3 | Barley | 0 | 0 | 0 | |
| 1/8 | 3 | Barley | 0 | 0 | 0 | |
| 1/4 | 3 | Barley | 20 | 0— | 0— | |
| 1/2 | 3 | Barley | 40 | 0— | 5— | |
| 1 | 3 | Barley | 97 | 18— | 13— | |
| 2 | 3 | Barley | 99 | 68— | 80— | |
| 4 | 3 | Barley | 100 | 88— | 85 | |

*Data reported is average of two replicates
— Denotes less than expected inhibition, i.e., "safening" occurred.

The compound of Example 3, Benzylamine-(α-methyl)-N-[4-(dichloromethylene)-1,3-dithiolan-2-ylidene]Hydrochloride was further tested as a seed treatment on several wheat varieties utilizing triallate as the herbicide according to the procedure of Example 56.

EXAMPLE 56

A toluene solution or suspension of the compound of Example 3 was applied to selected wheat varieties to obtain desired seed treatment concentrations. Untreated wheat seed and wheat seed treated with three concentrations of the compound of Example 3 were planted in 9¼×5¼×2¾ inch deep pans containing Ray silt loam soil. Cover layers of soil (450 gm) were sprayed with triallate, incorporated and placed on pre-seeded pans. The pans were given ¼ inch of overhead water and transferred to greenhouse benches where they were subirrigated as required during the remainder of the test. The results are summarized in Table VIII.

TABLE VIII

| Triallate Rate, Lb/A | Wheat Variety | % Wheat Inhibition* Seed Treatment Conc. (% W/W) | | | |
|---|---|---|---|---|---|
| | | 0 | 1/16 | 1/4 | 1 |
| 0 | Olaf semidwarf hard red spring | 0 | 0 | 0 | 0 |
| 1/16 | Olaf semidwarf hard red spring | 0 | 0 | 0 | 0 |
| 1/8 | Olaf semidwarf hard red spring | 3 | 0 | 0 | 0 |
| 1/4 | Olaf semidwarf hard red spring | 18 | 0 | 0 | 0 |
| 1/2 | Olaf semidwarf hard red spring | 78 | 0— | 0— | 0— |
| 1 | Olaf semidwarf hard red spring | 90 | 25— | 23— | 10— |
| 2 | Olaf semidwarf hard red spring | 100 | 60— | 53— | 40— |
| 0 | Nugaines white winter | 0 | 15 | 40 | 60 |
| 1/16 | Nugaines white winter | 0 | 0 | 35 | 63 |
| 1/8 | Nugaines white winter | 10 | 10 | 43 | 60 |
| 1/4 | Nugaines white winter | 53 | 10— | 25— | 45— |
| 1/2 | Nugaines white winter | 85 | 10— | 45— | 35— |
| 1 | Nugaines white winter | 93 | 23— | 50— | 55— |
| 2 | Nugaines white winter | 100 | 58— | 58— | 58— |
| 0 | Arthur 71 Soft red Winter | 0 | 0 | 0 | 0 |
| 1/16 | Arthur 71 Soft red Winter | 8 | 0 | 0 | 0 |
| 1/8 | Arthur 71 Soft red Winter | 33 | 0— | 0— | 0— |
| 1/4 | Arthur 71 Soft red Winter | 58 | 0— | 0— | 0— |
| 1/2 | Arthur 71 Soft red Winter | 98 | 0— | 0— | 15— |
| 1 | Arthur 71 Soft red Winter | 100 | 30— | 0— | 0— |
| 2 | Arthur 71 Soft red Winter | 100 | 93 | 18— | 5— |
| 0 | Eagle hard red winter | 0 | 0 | 0 | 5 |
| 1/16 | Eagle hard red winter | 0 | 0 | 0 | 0 |
| 1/8 | Eagle hard red winter | 3 | 0 | 0 | 0 |
| 1/4 | Eagle hard red winter | 53 | 0— | 0— | 0— |
| 1/2 | Eagle hard red winter | 99 | 0— | 0— | 0— |
| 1 | Eagle hard red winter | 100 | 5— | 0— | 5— |
| 2 | Eagle hard red winter | 100 | 53— | 23— | 25— |
| 0 | Rolette durum | 0 | 0 | 0 | 8 |
| 1/16 | " | 0 | 0 | 0 | 8 |
| 1/8 | " | 0 | 0 | 0 | 10 |
| 1/4 | " | 5 | 0 | 0 | 0 |
| 1/2 | " | 68 | 0— | 0— | 0— |
| 1 | " | 73 | 10— | 5— | 0— |
| 2 | " | 93 | 43— | 43— | 43— |
| 0 | Waldron hard red spring | 0 | 0 | 0 | 15 |
| 1/16 | Waldron hard red spring | 13 | 0 | 0 | 0— |
| 1/8 | Waldron hard red spring | 43 | 0— | 0— | 0— |
| 1/4 | Waldron hard red spring | 73 | 0— | 0— | 0— |
| 1/2 | Waldron hard red spring | 94 | 0— | 0— | 0— |
| 1 | Waldron hard red spring | 100 | 20— | 13— | 13— |
| 2 | Waldron hard red spring | 100 | 68— | 53— | 25— |

— Denotes less than expected inhibition, i.e., "safening"
*Average of 2 replicates

EXAMPLE 57

A toluene solution or suspension of the compound of Example 3, Benzylamine-α-methyl-N-[4-(dichloromethylene)-1,3-dithiolan-2-ylidene]hydrochloride was applied to wheat to obtain the desired seed treatment concentration. Untreated downy brome, green foxtail, wild oats and wheat seed along with wheat seed treated with three concentrations of the compound of Example 3 were planted in 9½×5¼×2¾ inch deep pans containing Ray silt loam soil. Triallate was applied to soil cover layers (450 gm) with the belt sprayer (20 gpa) and incorporated. The treated cover layers were placed on pre-seeded pans, the pans transferred to greenhouse benches and subirrigated.

TABLE IX

| Triallate Rate, Lb/A | % Wheat Inhibition Seed Treat. Conc. (% w/w) | | | | % Inhibition Grass Weeds | | |
|---|---|---|---|---|---|---|---|
| | 0 | 1/32 | 1/8 | 1/2 | FT | DB | WO |
| — | 0 | 0 | 0 | 0 | 0 | 0 | 0 |
| 1/32 | 0 | 0 | 0 | 0 | 0 | 20 | 80 |
| 1/16 | 0 | 0 | 0 | 0 | 10 | 60 | 85 |
| 1/8 | 15 | 0 | 0 | 0 | 25 | 95 | 95 |
| 1/4 | 45 | 0— | 0— | 0— | 55 | 95 | 99 |
| 1/2 | 90 | 0— | 0— | 0— | 65 | 100 | 99 |
| 1 | 98 | 30— | 0— | 10— | 70 | 100 | 100 |
| 2 | 99 | 90 | 45— | 35— | 75 | 100 | 100 |

FT = Green foxtail
DB = Downy brome
WO = Wild oats
— Denotes less than expected inhibition, i.e., "safening" occurred.

EXAMPLE 58

Dichloromethane solutions or suspensions of test chemicals were applied to sorghum to obtain desired seed treatment concentrations. Untreated crabgrass, foxtail, barnyardgrass and sorghum along with sorghum treated with three concentrations of a chemical were planted in 9½×5¼×2¾ inch deep pans containing Ray silt loam soil. Soil cover layers (450 gm) were placed on pre-seeded pans. Alachlor was applied to the soil surface with the belt sprayer (20 gpa). The pans were given ¼ inch of overhead water, transferred to greenhouse benches and sub-irrigated as required for the duration of the test. The results are summarized in Table X.

TABLE X

| Alachlor Rate, Lb/A | Seed Treatment Compound of Ex. No. | % Sorghum Inhibition Seed Treat. Conc. % w/w | | | | % Inhibition Grass Weeds[1] | | |
|---|---|---|---|---|---|---|---|---|
| | | 0 | 1/16 | 1/4 | 1 | CG | FT | BYG |
| 0 | 17 | 0 | 0 | 0 | 5 | 0 | 0 | 0 |
| 1/32 | ↓ | 85 | 0— | 0— | 10— | 60 | 98 | 98 |
| 1/16 | ↓ | 90 | 35— | 0— | 10— | 90 | 98 | 100 |
| 1/8 | ↓ | 95 | 80 | 0— | 0— | 95 | 99 | 100 |
| 1/4 | ↓ | 100 | 85 | 5— | 10— | 99 | 99 | 100 |
| 1/2 | ↓ | 98 | 85 | 50— | 20— | 99 | 100 | 100 |
| 1 | ↓ | 98 | 95 | 60— | 35— | 100 | 100 | 100 |
| 2 | ↓ | 99 | 95 | 70— | 30— | 100 | 100 | 100 |
| 0 | 20 | 0 | 5 | 10 | 95 | 0 | 0 | 0 |
| 1/32 | ↓ | 15 | 35 | 60 | 95 | 80 | 98 | 99 |
| 1/16 | ↓ | 30 | 0— | 25 | 100 | 85 | 99 | 99 |
| 1/8 | ↓ | 80 | 0— | 30— | 95 | 99 | 99 | 100 |
| 1/4 | ↓ | 95 | 75— | 50— | 90 | 99 | 100 | 100 |
| 1/2 | ↓ | 98 | 90 | 15— | 90 | 100 | 100 | 100 |
| 1 | ↓ | 99 | 95 | 45— | 100 | 100 | 100 | 100 |
| 2 | ↓ | 100 | 98 | 65— | 95 | 100 | 100 | 100 |
| 0 | 36 | 0 | 0 | 0 | 55 | 0 | 0 | 0 |
| 1/32 | ↓ | 5 | 0 | 0 | 50 | 40 | 98 | 98 |
| 1/16 | ↓ | 20 | 10 | 0 | 70 | 90 | 98 | 100 |
| 1/8 | ↓ | 40 | 0— | 0— | 50— | 90 | 98 | 100 |
| 1/4 | ↓ | 90 | 35— | 5— | 75— | 100 | 100 | 100 |
| 1/2 | ↓ | 100 | 45— | 15— | 75— | 100 | 100 | 100 |
| 1 | ↓ | 100 | 90 | 25— | 70— | 100 | 100 | 100 |
| 2 | ↓ | 100 | 98 | 60— | 80— | 100 | 100 | 100 |
| 0 | 3 | 0 | 0 | 0 | 0 | 0 | 0 | 0 |
| 1/32 | ↓ | 5 | 0 | 0 | 0 | 30 | 95 | 95 |
| 1/16 | ↓ | 65 | 55 | 20— | 0— | 45 | 100 | 98 |
| 1/8 | ↓ | 80 | 35— | 65 | 10— | 70 | 99 | 99 |

TABLE X-continued

| Alachlor Rate, Lb/A | Seed Treatment Compound of Ex. No. | % Sorghum Inhibition Seed Treat. Conc. % w/w | | | | % Inhibition Grass Weeds[1] | | |
|---|---|---|---|---|---|---|---|---|
| | | 0 | 1/16 | 1/4 | 1 | CG | FT | BYG |
| 1/4 | ↓ | 90 | 80 | 75 | 15— | 95 | 100 | 100 |
| 1/2 | ↓ | 90 | 95 | 75 | 30— | 95 | 100 | 100 |
| 1 | ↓ | 95 | 90 | 95 | 35— | 98 | 100 | 99 |
| 2 | ↓ | 99 | 98 | 90 | 70— | 99 | 100 | 100 |

[1] CG = Crabgrass
FT = Green Foxtail
BYG = Barnyardgrass
— Denotes less than expected inhibition, i.e., "safening" occurred.

EXAMPLE 59

Dichloromethane solutions or suspensions of the compound of Example 36 were applied to rice to obtain desired seed treatment concentrations. Untreated and treated rice were pregerminated for 2 days on moist towels. Plastic pots (4×4×3 inches deep) were filled with 2 inches of Ray silt loam soil. Barnyard grass was seeded into a shallow trench and covered with soil. Butachlor was applied to the soil surface with the belt sprayer (20 gpa). Rice was seeded into flooded pots. The water level was lowered to the soil surface after 24 hours and maintained at this level for 5 days after which the pots were reflooded for the duration of the test. The results are summarized in Table XI.

TABLE XI

| Butachlor Rate, lb/A | Seed Treatment Concentration % w/w | % Inhibition, Avg 2 Reps | |
|---|---|---|---|
| | | Water Seeded Rice | Barnyardgrass |
| 1/64 | — | 38 | 67 |
| 1/16 | — | 91 | 99 |
| 1/4 | — | 100 | 100 |
| — | 1/32 | 0 | 0 |
| 1/64 | 1/32 | 43 | 73 |
| 1/16 | 1/32 | 68— | 100 |
| 1/4 | 1/32 | 63— | 100 |
| — | 1/8 | 10 | 0 |
| 1/64 | 1/8 | 23— | 60 |
| 1/16 | 1/8 | 55— | 100 |
| 1/4 | 1/8 | 58— | 100 |
| — | 1/2 | 65 | 0 |
| 1/64 | 1/2 | 60— | 48 |
| 1/16 | 1/2 | 70— | 92 |
| 1/4 | 1/2 | 68— | 100 |

— Denotes less than expected inhibition, i.e., "safening" occurred.

The antidotes of the present invention may be combined with thiocarbamate or acetanilide herbicides as a tank mix and applied to soil planted with crop seed. Examples 57 and 58 and Tables XII and XIII describe this aspect of the invention in greater detail. The data shown in Tables XII and XIII is reported as % Inhibition; the % "safening effect" may be readily calculated by the use of the following formula: [% Inhibition of Crop Plant to Herbicide+% Inhibition of Crop Plant Due to Antidote]−% Inhibition of Crop Plant Due to Antidote/Herbicide Combination.

EXAMPLE 60

Wheat and several weed species were planted in 4×4×3 inch deep plastic pots containing Ray silt loam soil. The chemical combinations were applied as tank mixtures to soil cover layers with the belt sprayer (20 gpa). The treated cover layers were shaken in plastic bags to incorporate the chemicals. The cover layers were placed on preseeded pots, the pots transferred to a greenhouse bench and sub-irrigated. The results are summarized in Table XII.

gated as required during the remainder of the test. The results are summarized in Table XIII.

TABLE XII

| Triallate Rate lb/A | Compound of Example No. | Antidote Rate Lb/A | % Inhibition, Avg 2 Reps | | | | | | |
|---|---|---|---|---|---|---|---|---|---|
| | | | Wheat | Wild oats | Downy brome | Green foxtail | Ann. Rye-grass | Black grass | Barn-yard grass |
| 1/64 | — | — | 0 | 50 | 58 | | | | |
| 1/16 | — | — | 5 | 98 | 99 | 0 | | | |
| 1/4 | — | — | 68 | 100 | 100 | 20 | | | |
| 1 | — | — | 100 | 100 | 100 | 68 | | | |
| 0 | 3 | 1/4 | 0 | 0 | 0 | 0 | | | |
| 1/64 | ↓ | 1/4 | 0 | 73 | 60 | 0 | | | |
| 1/16 | ↓ | 1/4 | 8 | 98 | 100 | 0 | | | |
| 1/4 | ↓ | 1/4 | 43— | 100 | 100 | 18 | | | |
| 1 | ↓ | 1/4 | 100 | 100 | 100 | 60 | | | |
| 0 | ↓ | 1 | 0 | 0 | 0 | 0 | | | |
| 1/64 | ↓ | 1 | 0 | 88 | 60 | 0 | | | |
| 1/16 | ↓ | 1 | 0 | 99 | 100 | 0 | | | |
| 1/4 | ↓ | 1 | 15— | 100 | 100 | 5 | | | |
| 1 | ↓ | 1 | 98 | 100 | 100 | 82 | | | |
| 0 | ↓ | 4 | 0 | 0 | 0 | 0 | | | |
| 1/64 | ↓ | 4 | 0 | 55 | 10— | 0 | | | |
| 1/16 | ↓ | 4 | 0 | 100 | 68— | 0 | | | |
| 1/4 | ↓ | 4 | 0— | 100 | 100 | 10 | | | |
| 1 | ↓ | 4 | 85 | 100 | 100 | 18— | | | |
| 0 | 4 | 1/4 | 0 | 10 | 10 | 0 | | | |
| 1/64 | ↓ | 1/4 | 0 | 88 | 53 | 0 | | | |
| 1/16 | ↓ | 1/4 | 0 | 100 | 100 | 5 | | | |
| 1/4 | ↓ | 1/4 | 25— | 100 | 100 | 20 | | | |
| 1 | ↓ | 1/4 | 98 | 100 | 100 | 48— | | | |
| 0 | ↓ | 1 | 0 | 30 | 0 | 0 | | | |
| 1/64 | ↓ | 1 | 0 | 95 | 53 | 0 | | | |
| 1/16 | ↓ | 1 | 0 | 100 | 100 | 0 | | | |
| 1/4 | ↓ | 1 | 18— | 100 | 100 | 13 | | | |
| 1 | ↓ | 1 | 90 | 100 | 100 | 25— | | | |
| 0 | ↓ | 4 | 0 | 0 | 0 | 0 | | | |
| 1/64 | ↓ | 4 | 0 | 75 | 45 | 0 | | | |
| 1/16 | ↓ | 4 | 0 | 100 | 70— | 0 | | | |
| 1/4 | ↓ | 4 | 5— | 100 | 100 | 0— | | | |
| 1 | ↓ | 4 | 68— | 100 | 100 | 5— | | | |
| 0 | — | — | 0 | 0 | 0 | 0 | 0 | 0 | 0 |
| 1/32 | — | — | 0 | 85 | 65 | 0 | 65 | 33 | 0 |
| 1/16 | — | — | 0 | 97 | 98 | 0 | 93 | 85 | 0 |
| 1/8 | — | — | 38 | 99 | 99 | 8 | 98 | 94 | 0 |
| 1/4 | — | — | 63 | 100 | 100 | 28 | 99 | 100 | 0 |
| 1/2 | — | — | 95 | 100 | 100 | 50 | 100 | 100 | 0 |
| 0 | 3 | 1/8 | 0 | 0 | 0 | 0 | 0 | 0 | 0 |
| 1/32 | ↓ | 1/8 | 0 | 85 | 68 | 0 | 53 | 43 | 0 |
| 1/16 | ↓ | 1/8 | 0 | 98 | 93 | 0 | 89 | 83 | 0 |
| 1/8 | ↓ | 1/8 | 8— | 100 | 100 | 3 | 93 | 99 | 0 |
| 1/4 | ↓ | 1/8 | 63 | 100 | 100 | 30 | 99 | 99 | 0 |
| 1/2 | ↓ | 1/8 | 83 | 100 | 100 | 45 | 100 | 100 | 0 |
| 0 | 3 | 1/4 | 0 | 0 | 0 | 0 | 0 | 0 | 0 |
| 1/32 | ↓ | 1/4 | 0 | 75 | 63 | 0 | 50 | 20 | 0 |
| 1/16 | ↓ | 1/4 | 0 | 97 | 90 | 0 | 73— | 75 | 0 |
| 1/8 | ↓ | 1/4 | 10— | 99 | 100 | 0 | 90 | 99 | 0 |
| 1/4 | ↓ | 1/4 | 50 | 100 | 100 | 18 | 99 | 100 | 0 |
| 1/2 | ↓ | 1/4 | 83 | 100 | 100 | 35 | 100 | 100 | 0 |
| 0 | 3 | 1/2 | 0 | 0 | 0 | 0 | 0 | 0 | 0 |
| 1/32 | ↓ | 1/2 | 0 | 90 | 53 | 0 | 45— | 28 | 0 |
| 1/16 | ↓ | 1/2 | 0 | 97 | 85 | 0 | 35— | 53— | 0 |
| 1/8 | ↓ | 1/2 | 0— | 98 | 95 | 0 | 70— | 70— | 0 |
| 1/4 | ↓ | 1/2 | 20— | 99 | 100 | 8— | 94 | 99 | 0 |
| 1/2 | ↓ | 1/2 | 60— | 100 | 100 | 20— | 99 | 100 | 0 |

— Denotes less than expected inhibition, i.e., "safening" occurred.

EXAMPLE 61

Sorghum, crabgrass, green foxtail and barnyardgrass were planted in 4×4×3 inch deep plastic pots containing Ray silt loam soil. Soil cover layers were placed on the preseeded pots. A combination of alachlor and the compound of Example 17 was applied as a tank mixture to the soil surface with the belt sprayer (20 gpa). The pots were given ¼ inch of overhead water and transferred to greenhouse benches. The pots were subirrigated as required during the remainder of the test. The results are summarized in Table XIII.

TABLE XIII

| Alachlor Rate, Lb/A | Antidote Rate Lb/A | % Inhibition, Avg. 2 reps | | | |
|---|---|---|---|---|---|
| | | Sorghum | Crabgrass | Green Foxtail | Barnyard Grass |
| 1/32 | — | 0 | 18 | 88 | 60 |
| 1/8 | — | 10 | 63 | 93 | 97 |
| 1/2 | — | 68 | 94 | 99 | 100 |
| 2 | — | 85 | 98 | 99 | 100 |
| 0 | 1/8 | 0 | 0 | 0 | 0 |
| 1/32 | 1/8 | 0 | 18 | 75 | 43 |
| 1/8 | 1/8 | 8 | 55 | 98 | 97 |
| 1/2 | 1/8 | 50 | 83 | 99 | 100 |

TABLE XIII-continued

| Alachlor Rate, Lb/A | Antidote Rate Lb/A | % Inhibition, Avg. 2 reps | | | |
|---|---|---|---|---|---|
| | | Sorghum | Crabgrass | Green Foxtail | Barnyard Grass |
| 2 | 1/8 | 96 | 98 | 100 | 100 |
| 0 | 1/2 | 0 | 0 | 0 | 15 |
| 1/32 | 1/2 | 0 | 13 | 73 | 15— |
| 1/8 | 1/2 | 5 | 65 | 95 | 98 |
| 1/2 | 1/2 | 45— | 88 | 99 | 100 |
| 2 | 1/2 | 94 | 98 | 100 | 100 |
| 0 | 2 | 0 | 0 | 0 | 0 |
| 1/32 | 2 | 0 | 13 | 82 | 45 |
| 1/8 | 2 | 0 | 50 | 97 | 99 |
| 1/2 | 2 | 58 | 85 | 99 | 100 |
| 2 | 2 | 75 | 97 | 99 | 100 |

— Denotes less than expected inhibition, i.e., "safening" occurred.

Several of the compounds of the invention were tested on water-seeded rice plants utilizing butachlor herbicide following the procedure of Example 62.

EXAMPLE 62

Plastic pots (4×4×3 inches deep) were filled with 2 inches of Ray silt loam soil. The combination treatments were applied sequentially to the soil surface with the belt sprayer (20 gpa). Pre-soaked rice (2 day duration) was seeded into flooded pots. The water level was lowered to the soil surface after 24 hours and maintained at this level for 5 days after which the pots were reflooded for the duration of the test. The results obtained when water-seeded rice was treated in the manner described above are summarized in Table XIV.

TABLE XIV

| Compound of Example No. | Rate of Herbicide (lb/A) | Rate of Antidote (lb/A) | Safening Effect |
|---|---|---|---|
| 3 | 1/64 | 1/2 | * |
| ↓ | 1/16 | ↓ | 35 |
| ↓ | 1/4 | ↓ | * |
| 4 | 1/64 | 1/2 | 26 |
| ↓ | 1/16 | ↓ | 23 |
| ↓ | 1/4 | ↓ | * |
| 36 | 1/64 | 1/2 | 26 |
| ↓ | 1/16 | ↓ | 60 |
| ↓ | 1/2 | ↓ | * |
| 5 | 1/32 | 1 | * |
| ↓ | 1/8 | ↓ | 44 |
| ↓ | 1/2 | ↓ | 37 |
| 46 | 1/16 | 1/2 | 32 |
| ↓ | 1/4 | ↓ | * |
| ↓ | 1 | ↓ | * |

*Safening effect was between 0 and 19.

Compounds of Examples 17, 20, 31, 34, 43 and 51 exhibited less than 20 units of safening when tested at 1/64, 1/16 and ¼ pounds per acre.

The above examples illustrate that the 2-imino-1,3-dithio and 1,3-oxathio derivatives of the present invention are useful in reducing herbicidal injury to crop plants, for example, sorghum, rice and wheat. The safening agents may be applied to the plant locus as a mixture, i.e., a mixture of a herbicidally effective amount of thiocarbamate or acetanilide herbicide and a safening effective amount of safening agent, or sequentially, i.e., the plant locus may be treated with an effective amount of the herbicide followed by a treatment with the safening agent or vice versa. The ratio of herbicide to safening agent may vary depending upon the crop to be protected, weeds to be inhibited, herbicide used, etc., but normally a herbicide to safening agent ratio ranging from 1:25 to 25:1 (preferably 1:5 to 5:1) parts by weight may be employed.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant locus, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention to plants can be accomplished by incorporating the compositions in the soil or other media.

The above examples also illustrate that the crop may be protected by treating the crop seed with an effective amount of safening agent prior to planting. Generally, small amounts of safening agent are required to treat such seeds. A weight ratio of as little as 0.031 parts of safener per 1000 parts of seed may be effective. The amount of safener utilized in treating the seed may be increased if desired. Generally, however, a weight ratio of safening agent to seed weight may range from 0.1 to 10.0 parts of safening agent per 1000 parts of seed. The determination of the effective amount of safening agent required is well within the skill of the art.

Since only a very small amount of active safening agent is usually required for the seed treatment, the compound preferably is formulated as a powder or an emulsifiable concentrate which can be diluted with water by the seed treater for use in the seed treating apparatus. Of course, under certain conditions, it may be desirable to dissolve the safening agent in an organic solvent for use as a seed treatment or the pure compound alone may be used under properly controlled conditions.

There are thus also provided by this invention novel seed treating compositions containing one or more of the described active safening agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and may be either pure compounds, mixtures of compounds of the same general groups, or they may be mixtures of compounds of different classes. Typical satisfactory surface-active agents which may be used are alkali metal higher alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8-18 carbon atoms, long chain quaternary ammonium compounds, sodium salts of petroleum-derived alkylsulfonic acids, polyethylene sorbitan monooleate, alkylaryl polyether alcohols, water-soluble lignin sulfonate salts, alkali-casein compositions, long chain alcohols usually containing 10-18 carbon atoms, and condensation products of ethylene oxide with fatty acids, alkylphenols and mercaptans.

While the compounds of the present invention, which are described hereinabove, generally safen crop plants, especially cereal crop plants, against the herbicidal effect of thiocarbamate and acetanilide herbicides, those skilled in the art will appreciate, from the biological data reported above, that various of the compounds of the present invention are most advantageously employed in a method of safening specific crop plants against either thiocarbamate or acetanilide herbicides. The following specific embodiments of the present invention are expressly contemplated herein (the limitations previously noted in the description of the invention likewise apply to the specific embodiments):

A. A method of reducing injury to rice, sorghum and wheat injured by thiocarbamate herbicides, especially triallate, using a safening effective amount of the compounds of the formula:

R-N=A or an agriculturally acceptable acid addition salt thereof, wherein R is lower alkyl,

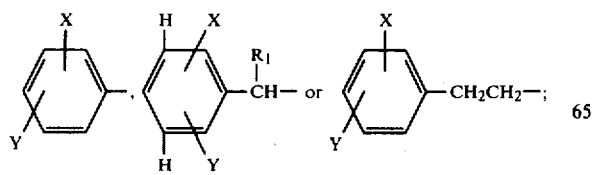

$R_1$ is hydrogen, methyl, ethyl or isopropyl;
X and Y are independently equal to lower alkyl, lower alkoxy or halogen;

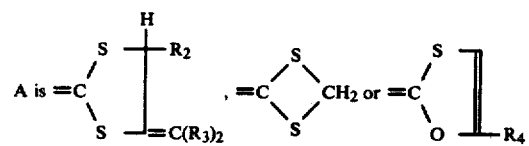

$R_2$ is hydrogen or methyl;
$R_3$ is hydrogen or chloro;
$R_4$ is hydrogen, methyl or phenyl.

b. A method or reducing injury to sorghum plants injured by acetanilide herbicides, especially alachlor, using a safening effective amount of compounds of the formula

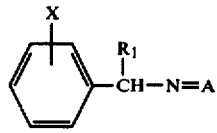

or an agriculturally acceptable acid addition salt thereof, wherein $R_1$ is hydrogen or methyl; X is hydrogen, lower alkyl or lower alkoxy;

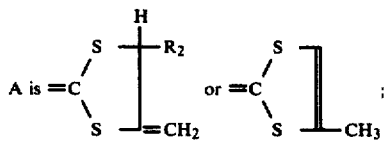

$R_2$ is hydrogen or methyl;
provided that when A is

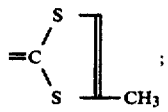

X must equal hydrogen.

C. A method of reducing injury to rice plants injured by acetanilide herbicides, especially butachlor, using a safening effective amount of compounds of the formula:

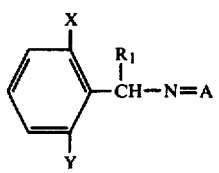

or an agriculturally acceptable acid addition salt thereof, wherein $R_1$ is hydrogen, methyl, ethyl, isopropyl, butyl or isobutyl; X and Y are independently equal to lower alkyl, lower alkoxy or halogen;

A is 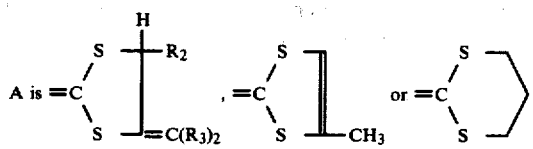

R$_2$ is hydrogen or methyl; R$_3$ is hydrogen or chloro; provided that when A is

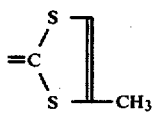

R$_1$ cannot equal isopropyl.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of reducing injury to rice sorghum and wheat due to the application thereof of alachlor and butachlor which comprises applying to the plant locus a safening effective amount of a compound having the formula

R-N=A or an agriculturally acceptable acid addition salt thereof, wherein R is hydrogen, or

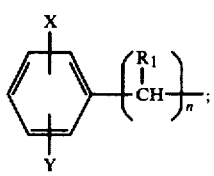

R$_1$ is hydrogen or lower alkyl; X and Y independently equal hydrogen, lower alkyl, lower alkoxy or Cl; n is 0, 1, 2 or 3; A is

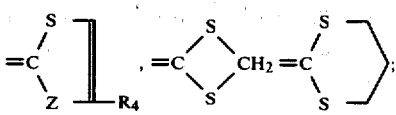

R$_4$ is hydrogen, methyl or phenyl; Z is oxygen or sulfur; provided that when n is 1 and A is

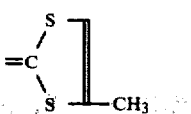

R$_1$ cannot equal n-propyl or isobutyl.

2. A method according to claim 1 wherein said agriculturally acceptable acid addition salt is the hydrochloride salt.

3. A method according to claim 1 wherein in said compound n is 0.

4. A method according to claim 1 wherein in said compound R is

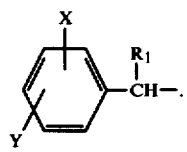

5. A method according to claim 4 wherein R$_1$ is methyl and X and Y are hydrogen.

6. A method according to claim 1 wherein in said compound A is

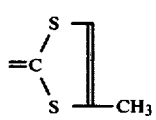

7. A method according to claim 1 wherein R is

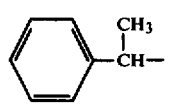

and A is

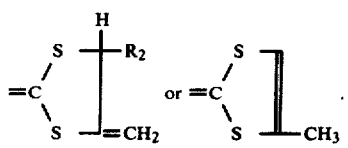

8. A method according to claim 7 wherein said agriculturally acceptable acid addition salt is the hydrochloride salt.

9. A method according to claim 7 wherein said crop plant is wheat.

10. A method according to claim 9 wherein said compound is

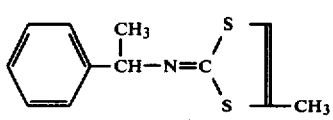

or its hydrochloride salt.

11. A method according to claim 9 wherein said compound is

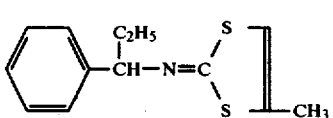

or its hydrochloric salt.

12. A method according to claim 13 wherein R is lower alkyl,

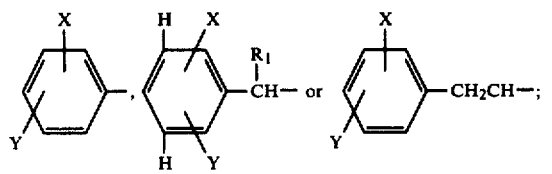

R₁ is hydrogen, methyl, ethyl or isopropyl; A is

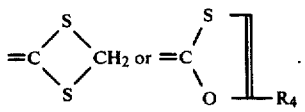

13. A method according to claim 12 wherein R is

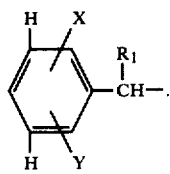

14. A method according to claim 13 wherein R₁ is methyl.

15. A method according to claim 12 wherein X and Y are independently hydrogen, methyl, methoxy or chlorine.

16. A method according to claim 12 wherein the agriculturally acceptable acid addition salt is the hydrochloride salt.

17. A method according to claim 1 wherein said crop plant is sorghum.

18. A method according to claim 17 wherein said herbicide is alachlor.

19. A method according to claim 18 wherein R is

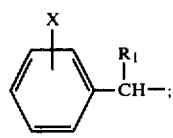

R₁ is hydrogen or methyl; X is hydrogen, lower alkyl or lower alkoxy; A is

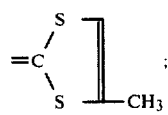

provided that X must equal hydrogen.

20. A method according to claim 19 wherein R₁ is methyl.

21. A method according to claim 20 wherein X is hydrogen.

22. A method according to claim 21 wherein A is

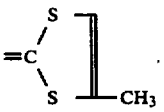

23. A method according to claim 19 wherein the agriculturally acceptable acid addition salt is the hydrochloride salt.

24. A method according to claim 1 wherein said crop plant is rice.

25. A method according to claim 24 wherein said herbicide is butachlor.

26. A method according to claim 25 wherein R is

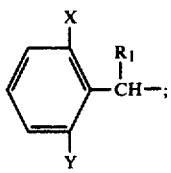

R₁ is hydrogen, methyl, ethyl, isopropyl, butyl or isobutyl; A is

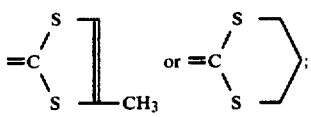

provided that when A is

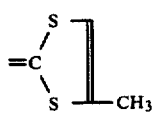

R₁ cannot equal isopropyl.

27. A method according to claim 26 wherein R₁ is methyl.

28. A method according to claim 27 wherein X and Y are hydrogen.

29. A method according to claim 28 wherein A is

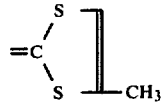

30. A method according to claim 26 wherein the agriculturally acceptable acid addition salt is the hydrochloride salt.

31. A mixture which comprises a herbicidally effective amount of alachlor or butachlor and a safening effective amount of a compound of the formula

R-N=A or an agriculturally acceptable acid addition salt thereof, wherein R is hydrogen, or

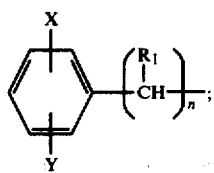

$R_1$ is hydrogen or lower alkyl; X and Y independently equal hydrogen, lower alkyl, lower alkoxy, lower alkoxy or Cl; n is 0, 1, 2 or 3; A is

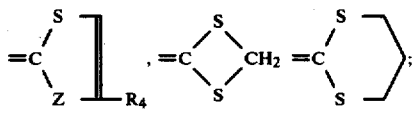

$R_4$ is hydrogen, methyl or phenyl; Z is oxygen or sulfur; provided that when n is 1 and A is

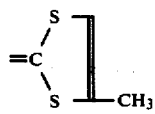

$R_1$ cannot equal n-propyl or isobutyl.

32. A mixture according to claim 31 wherein said acetanilide herbicide is alachlor.

33. A mixture according to claim 31 wherein said acetanilide herbicide is butachlor.

34. A mixture according to claim 31 wherein said agriculturally acceptable acid addition salt is the hydrochloride salt.

35. A mixture according to claim 31 wherein n is 0.

36. A mixture according to claim 31 wherein R is

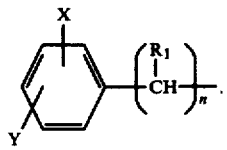

37. A mixture according to claim 36 wherein $R_1$ is methyl and n is 1.

38. A mixture according to claim 37 wherein X and Y are hydrogen.

39. A mixture according to claim 31 wherein A is

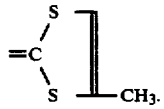

* * * * *